US009402743B2

(12) United States Patent
Orphanos et al.

(10) Patent No.: US 9,402,743 B2
(45) Date of Patent: Aug. 2, 2016

(54) MEDICAL IMPLANT DRIVER WITH DEPTH-LIMITING FEATURE

(71) Applicant: DePuy Mitek, LLC, Raynham, MA (US)

(72) Inventors: Stephen J. Orphanos, Bridgewater, MA (US); Scott Presbrey, Slatersville, RI (US)

(73) Assignee: DEPUY MITEK, LLC, Raynham, MA (US)

( * ) Notice: Subject to any disclaimer, the term of this patent is extended or adjusted under 35 U.S.C. 154(b) by 295 days.

(21) Appl. No.: 14/036,872

(22) Filed: Sep. 25, 2013

(65) Prior Publication Data

US 2015/0088148 A1 Mar. 26, 2015

(51) Int. Cl.
*A61B 17/92* (2006.01)
*A61F 2/46* (2006.01)
*A61F 2/08* (2006.01)

(52) U.S. Cl.
CPC . *A61F 2/46* (2013.01); *A61B 17/92* (2013.01); *A61F 2/0805* (2013.01); *A61B 2017/922* (2013.01); *A61B 2090/033* (2016.02); *A61F 2002/0882* (2013.01)

(58) Field of Classification Search
CPC ........ A61B 17/92; A61B 17/921; A61B 2/46; A61B 17/88
USPC .................................................... 606/99, 104
See application file for complete search history.

(56) References Cited

U.S. PATENT DOCUMENTS

| | | | |
|---|---|---|---|
| 5,484,094 A | 1/1996 | Gupta | |
| 5,843,115 A | 12/1998 | Morejon | |
| 5,980,558 A | 11/1999 | Wiley | |
| 6,681,869 B2 | 1/2004 | Wursch et al. | |
| 6,695,192 B1 | 2/2004 | Kwok | |
| 6,866,177 B1 | 3/2005 | Chen | |
| 6,929,647 B2 | 8/2005 | Cohen | |
| 7,055,729 B2 | 6/2006 | Taylor et al. | |
| 7,299,961 B2 | 11/2007 | Stavig, Jr. et al. | |
| 7,316,342 B2 | 1/2008 | Chen | |
| 7,318,546 B2 | 1/2008 | Segura et al. | |
| 7,341,172 B2 | 3/2008 | Moore et al. | |
| 7,513,404 B2 | 4/2009 | Shkolnikov et al. | |
| 8,425,532 B2 * | 4/2013 | Flom .................. | A61B 17/3421 606/104 |
| 2008/0269764 A1 * | 10/2008 | Blain .................. | A61B 17/025 606/99 |
| 2009/0163963 A1 * | 6/2009 | Berrevoets .......... | A61B 17/7082 606/86 A |
| 2012/0130387 A1 * | 5/2012 | Simpson ............... | A61F 2/4611 606/104 |
| 2012/0271421 A1 * | 10/2012 | Lee ....................... | A61F 2/4611 623/17.16 |

OTHER PUBLICATIONS

[No Author Listed] Rigidfix: ACL Cross Pin System. DePuy Mitek. Feb. 2000. 6 pages.

* cited by examiner

*Primary Examiner* — Christopher Beccia

(57) ABSTRACT

Devices, systems, and methods for driving an implant into bone to a predetermined depth are described herein. In one embodiment, a medical driver tool is provided that includes a housing having a proximal end configured to receive an impacting force, an elongate shaft extending distally from the housing and having a distal tip configured to drive an implant into bone, and a release mechanism coupled between the housing and the elongate shaft. The release mechanism can have an engaged position in which the elongate shaft is axially immovable relative to the housing and a disengaged position in which the elongate shaft is axially movable relative to the housing. The release mechanism can be configured to move from the engaged position to the disengaged position in response to a force applied to move at least a portion of the release mechanism proximally relative to the housing.

19 Claims, 21 Drawing Sheets

US 9,402,743 B2

MEDICAL IMPLANT DRIVER WITH DEPTH-LIMITING FEATURE

FIELD

This application relates generally to surgical procedures and, more particularly, to devices, systems, and methods for controlling the depth of insertion of a medical implant.

BACKGROUND

Many surgical procedures involve driving an implant into bone. Various implants can be driven into bone at any of number of locations within a patient's body for a variety of purposes. For example, when repairing tears in the cruciate ligaments of the knee, one common procedure involves driving one or more cross-pins into a patient's femur to secure a ligament graft within a bone tunnel formed in the femur. DePuy Mitek, by way of further example, provides its RIGIDFIX absorbable pins for use in this type of procedure. As shown in FIGS. 1A and 1B, the RIGIDFIX absorbable pins 102 can be used to secure either a soft tissue graft 104 (shown in FIG. 1A) or a so-called bone-tendon-bone graft 106 (shown in FIG. 1B) within a bone tunnel formed in a patient's femur 108.

As shown in FIG. 2, the pins can be driven into the patient's femur 108 through a delivery cannula 202 that is inserted partway into the femur at the correct alignment. After the delivery cannula 202 is inserted, a pin 102 can be placed into the delivery cannula 202 at its proximal end and driven into the bone using a driver shaft 302 and an impacting tool, as shown in FIG. 3. A number of different impacting tools can be used, including, for example, a hammer.

In many procedures, an implant being driven into bone in this manner must be delivered to a particular depth or undesirable complications may result. In the case of cruciate ligament repair using cross-pins, for example, it can be desirable to drive the pins 102 to a depth that leaves an amount of clearance between a distal end of the pins 102 and the outer surface of the lateral cortex of the femur 108, as shown in FIG. 4. Overdriving the pins 102 can result in too little clearance between the distal end of the pins 102 and the outer surface of the lateral cortex, or even protrusion of the pin through the outer surface of the femur, as shown in FIG. 5.

Accordingly, there is a need for novel devices, systems, and methods for controlling the depth of insertion of a medical implant. In particular, there is a need for improved devices, systems, and methods for both indicating to a user that a predetermined insertion depth has been reached and preventing further insertion of the implant even if the indication is ignored.

SUMMARY

The present invention generally provides devices, systems, and methods for controlling the depth of insertion of a medical implant into bone. This can be accomplished using a driver tool having a depth-limiting feature that prevents a user from over-driving an implant. The depth-limiting feature can both provide a visual indication to a user that a predetermined depth has been reached and prevent over-driving of the implant if the indication is ignored. The devices, systems, and methods described herein can be utilized in a variety of procedures and locations in the body where controlling the depth of insertion of an implant is important to prevent undesirable complications.

In one aspect, a medical driver tool is provided that includes a housing having proximal and distal ends, the proximal end being configured to receive an impacting force. The impacting force can be provided from a variety of tools, including, e.g., a hammer. The medical driver tool can further include an elongate shaft extending at least partially through the housing and extending distally from the housing. Further, the elongate shaft can have a distal tip configured to drive an implant into bone. The medical driver tool can also include a release mechanism coupled between the housing and the elongate shaft. The release mechanism can have an engaged position in which the elongate shaft is axially immovable relative to the housing, and a disengaged position in which the elongate shaft is axially movable relative to the housing. The release mechanism can be configured to move from the engaged position to the disengaged position in response to a force applied to move at least a portion of the release mechanism proximally relative to the housing.

The medical driver tool can have a number of different sizes, component configurations, or additional features, all of which are considered within the scope of the present invention. For example, the release mechanism can include a variety of mechanical configurations that allow for selective movement of the elongate rod relative to the housing. In one embodiment, the release mechanism can include a plurality of retaining balls spaced radially around the elongate shaft and seated within a detent formed in an outer surface of the elongate shaft. As explained in more detail below, selectively constraining the retaining balls within the detent formed in the elongate shaft can control its ability to move relative to the housing of the driver tool.

In other embodiments, the release mechanism can include a plurality of biased retaining pins that engage a shoulder formed on the elongate shaft. The retaining pins can be biased toward the elongate shaft to maintain engagement with the shoulder, and selective movement of the pins against the biasing force can allow the shaft to move relative to the housing of the driver tool.

In still other embodiments, the release mechanism can include a plurality of pivoting retaining pawls that engage a shoulder formed on the elongate shaft. In such an embodiment, rotating the pawls about a pivoting axis can allow the elongate shaft to move relative to the housing of the driver tool.

In some embodiments, the release mechanism can also include a trigger element extending distally from the housing. The trigger element can be movable relative to the housing and can be coupled to various other components of the release mechanism, e.g., the retaining balls bearings, pins, or pawls described above. The trigger element can be configured to contact a surface of the patient (e.g., a skin surface) or another component (e.g., a delivery cannula) such that the surface causes the trigger element to move proximally relative to the housing, thereby moving the release mechanism from the engaged position to the disengaged position.

In other embodiments, the release mechanism can be configured to move the elongate shaft proximally relative to the housing when moving from the engaged position to the disengaged position. This can be accomplished, for example, by biasing the elongate shaft in the direction of the proximal end of the housing using a coil spring or other biasing member. Accordingly, when the release mechanism is moved to the disengaged position, the biasing member can move the elongate shaft proximally relative to the housing. The biasing member can be selected to provide any desired length of movement of the elongate shaft. For example, in some embodiments, the elongate shaft can be moved proximally by about 10 mm. In certain embodiments, this distance can be sufficient to prevent the implant from being driven further into bone even if a user provides additional impacting force after the release mechanism is moved to the disengaged position.

In another aspect, a medical implant and delivery system is provided that includes a biocompatible implant configured to be implanted in bone. Any of a variety of implants can be utilized. In some embodiments, for example, the biocompatible implant can be a pin used to fix a graft within a bone tunnel. The system can also include a driver tool having a housing with proximal and distal ends, and the proximal end can be configured to receive an impacting force. The driver tool can also include an elongate shaft extending at least partially through the housing and extending distally from the housing, and the elongate shaft can have a distal tip configured to drive the biocompatible implant into bone. The driver tool can further include a release mechanism coupled between the housing and the elongate shaft. The release mechanism can be configured to move from an engaged position in which the elongate shaft is axially immovable relative to the housing to a disengaged position in which the elongate shaft is axially movable relative to the housing in response to a force applied to move at least a portion of the release mechanism proximally relative to the housing.

In some embodiments, the system can further include a delivery cannula configured to receive the biocompatible implant and a distal portion of the elongate shaft of the driver tool. In use, a distal portion of the delivery cannula can be implanted in bone and the implant can be placed within a proximal portion of the delivery cannula. A distal portion of the elongate shaft of the driver tool can then be placed within the delivery cannula and an impacting force can be applied to a proximal portion of the driver tool to drive the implant through the delivery cannula and into bone.

In some embodiments, the system can further include an impactor configured to impart a force to the proximal end of the driver tool housing or to a proximal end of the elongate shaft extending therethrough. The impactor can be any of a variety of tools known in the art. In some embodiments, for example, the impactor can be a hammer.

The release mechanism of the driver tool can include any of the possible configurations described above. For example, in some embodiments the release mechanism can include a trigger element configured to contact a proximal end of the delivery cannula. The delivery cannula can in turn move the trigger element proximally relative to the housing of the driver tool and cause the release mechanism to move from the engaged position to the disengaged position.

The release mechanism can selectively restrain the relative movement of the elongate shaft and housing using a number of different configurations. In some embodiments, for example, the release mechanism can include a plurality of retaining balls spaced radially around the elongate shaft and seated within a detent formed in an outer surface of the elongate shaft. Selectively constraining the movement of the retaining balls out of the detent in the elongate shaft can prevent the shaft from moving relative to the housing. In other embodiments, the release mechanism can include a plurality of biased retaining pins that engage a shoulder formed on the elongate shaft. In still other embodiments, the release mechanism can include a plurality of pivoting retaining pawls that engage a shoulder formed on the elongate shaft.

In another aspect, a method for implanting an implant in bone is provided that includes applying a driving force to a proximal end of a housing on a driver tool to thereby drive an elongate shaft of the driver tool distally toward bone. Further, when the implant is driven to a predetermined depth, a release mechanism of the driver tool is actuated to allow the elongate shaft to slide proximally relative to the housing.

In some embodiments, actuation of the release mechanism can occur in response to application of a force to a trigger element of the release mechanism to move the trigger element proximally relative to the housing. In certain embodiments, actuation of the release mechanism can occur in response to the trigger element contacting a proximal end of a delivery cannula or other component. In still other embodiments, the release mechanism can be actuated by the trigger element contacting a skin surface of the patient. In some embodiments, actuating the release mechanism can also include moving the elongate shaft proximally relative to the housing. The distance moved by the elongate shaft can be set as desired by including, for example, a properly sized biasing member, such as a coil spring. Any of a variety of distances can be selected according to the intended use of the device and implemented by utilizing an appropriately sized biasing member. In some embodiments, for example, the distance moved by the elongate shaft can be in a range of about 1 mm to about 100 mm, though even larger distances can be used if, for example, the elongate shaft is particularly long. In other embodiments, the distance moved by the elongate shaft can be in a range of about 1 mm to about 50 mm, about 1 mm to about 25 mm, about 1 mm to about 15 mm, or about 1 mm to about 10 mm. By way of further example, in some embodiments, the distance moved by the elongate shaft can be about 10 mm.

In still other embodiments, applying a driving force can include impacting a proximal end of the housing, or a proximal end of the elongate shaft extending through the housing, with a hammer. Other tools known in the art can also be used to provide a driving force to the tool.

Those skilled in the art will appreciate other alternatives or variations that can be used in combination with the devices, systems, and methods described herein. All of these are considered within the scope of the present invention.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Described herein are devices, systems, and methods for controlling the depth of insertion of a medical implant into bone. In general, devices according to the teachings of the present invention can be employed in place of the elongate shafts often used to drive implants into bone, e.g., the driver shaft 302 described above. The devices described herein can include a depth-limiting feature that prevents a user from over-driving an implant into bone. The depth-limiting feature can both provide a visual indication to a user that a predetermined depth has been reached and prevent over-driving of the implant if the indication is ignored.

Figure 3:
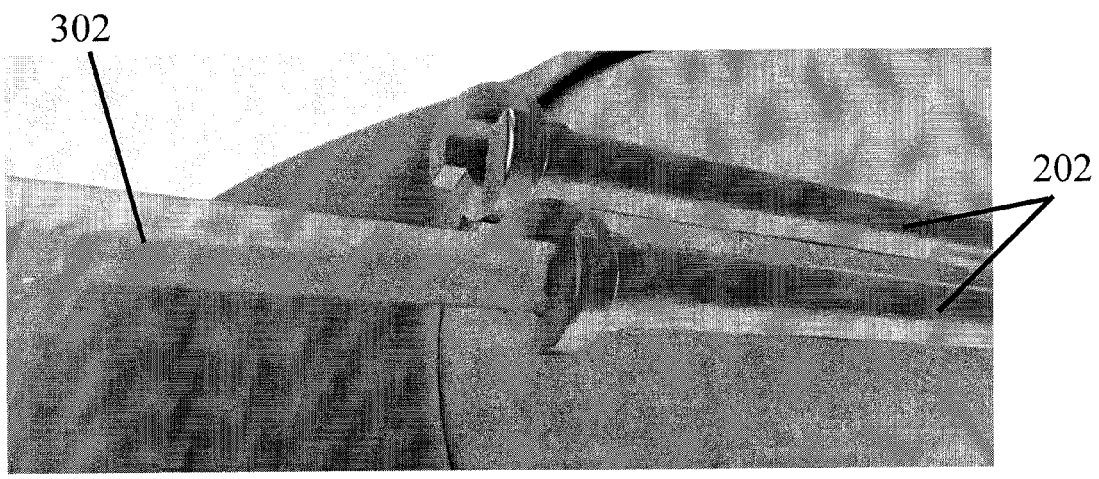
FIG. 3 is an illustration of a prior art delivery cannula and driver shaft.
Figure 4:
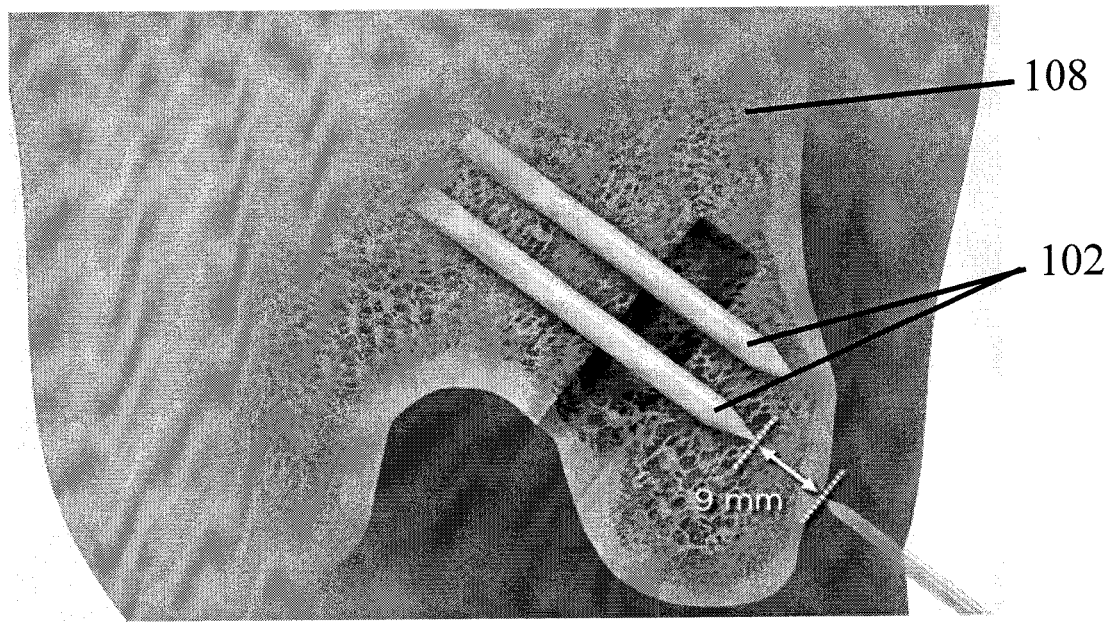
FIG. 4 is an illustration of placement of a prior art pin within a knee.
Figure 5:
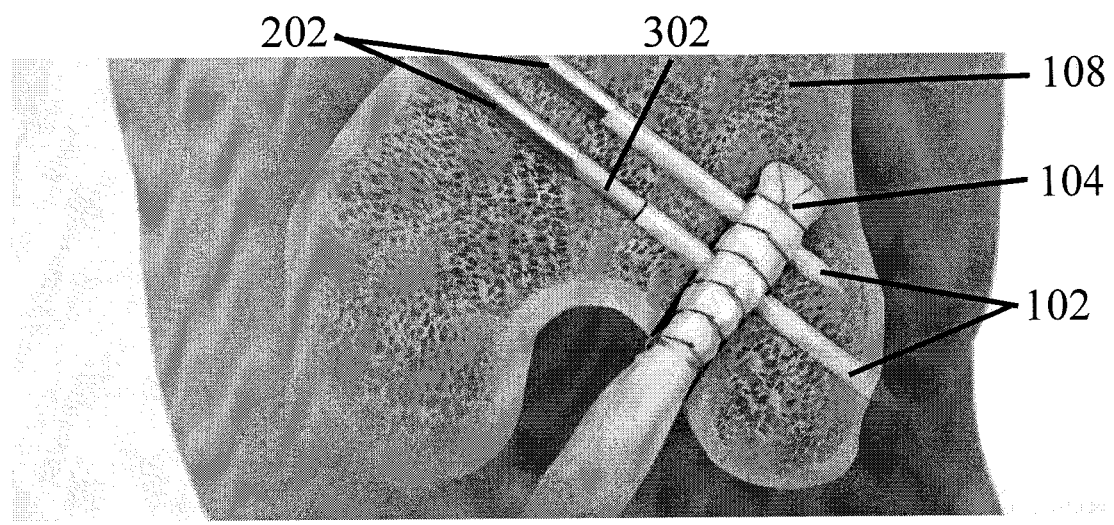
FIG. 5 is an illustration of over-driving a prior art pin within a knee.

The devices, systems, and methods described herein can be utilized in a variety of procedures and locations in the body where controlling the depth of insertion of an implant is important to prevent undesirable complications. As mentioned above, one such procedure is securing a cruciate ligament (e.g., the Anterior Cruciate Ligament or ACL) graft within a bone tunnel in a patient's femur. In this procedure, a distal portion of one or more delivery cannulas 202 can be inserted partway (e.g., about 4 cm in some embodiments) into a patient's femur in alignment with a bone tunnel formed therein. A biocompatible implant, i.e., a pin 102, and a driver shaft 302 can then be placed within the delivery cannula 202. The pin 102 can be driven into the femur (and through the bone tunnel and graft positioned therein) by delivering an impacting force to the proximal end of the driver shaft 302 that extends from a proximal end of the delivery cannula 202, as shown in FIG. 3. As mentioned above, it can be desirable to leave an amount of clearance between a distal end of the pin 102 and the outer surface of the lateral cortex of the femur 108. In some embodiments, for example, it can be desirable to drive the pin 102 to a depth that leaves at least about 2 mm of clearance between the distal end of the pin 102 and the outer surface of the lateral cortex of the femur 108. In other embodiments, the desired clearance can be larger than 2 mm based on the positioning of the femoral tunnel, the particular anatomy of the patient's lateral cortex, the implant engagement depth, etc. By way of further example, clearance of about 9 mm between a distal end of the pin 102 and the outer surface of the femoral lateral cortex is shown in FIG. 4. Over-driving the pin 102 can result in clearance below 9 mm (or whatever other desired clearance is selected), or even protrusion of the distal end of the cross-pin from the femur, as shown in FIG. 5. Unfortunately, surgeons often over-drive the pin 102 due to the fact that there is no indication that the correct depth has been reached. As a result, surgeons often add one or more taps from a hammer or other impacting tool beyond what is necessary to insure against under-driving the implant.

Figure 6A:
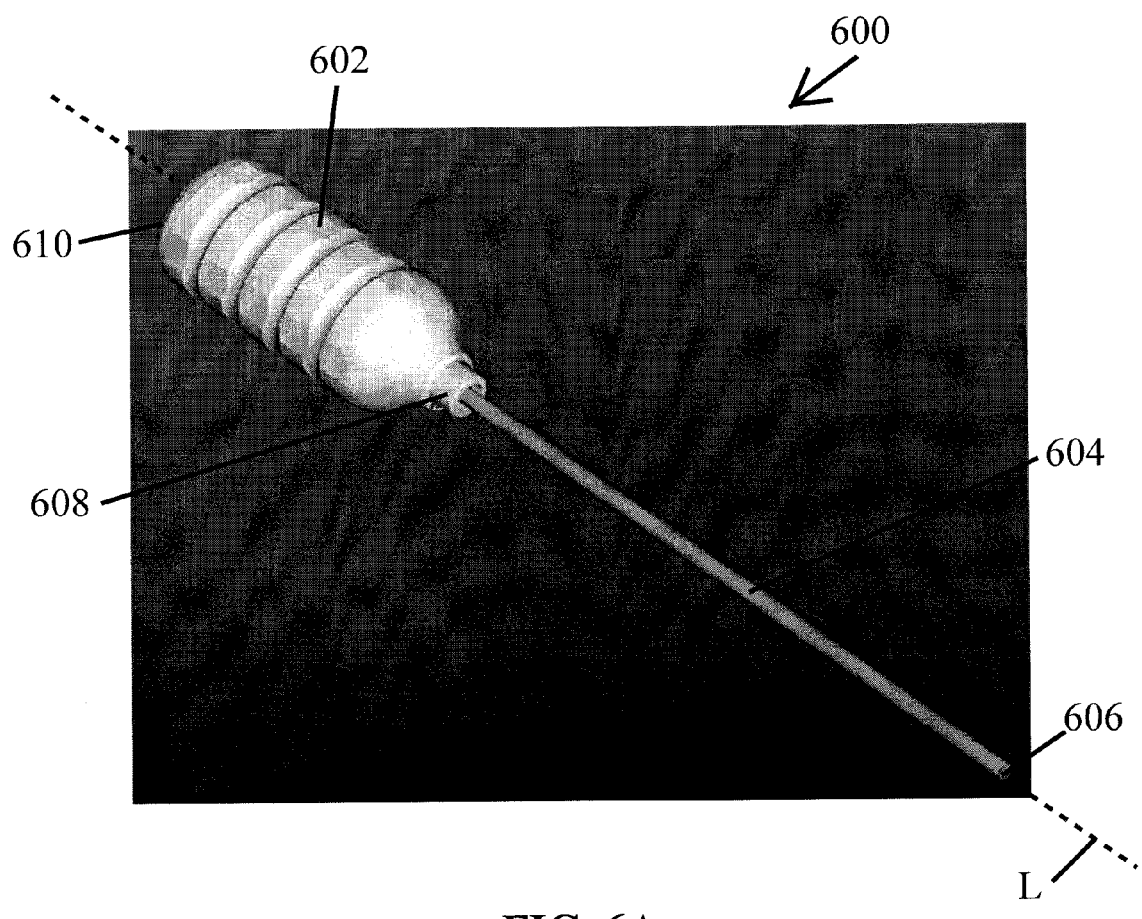
FIG. 6A is an illustration of one embodiment of a medical driver tool in a first configuration.

To prevent over-driving of the implant and provide better feedback regarding insertion depth, one embodiment of a medical driver tool 600 can be employed in place of the driver shaft 302. As shown in FIG. 6A, the medical driver tool 600 can include a housing 602 having proximal and distal ends, and an elongate shaft 604 extending at least partially through the housing and extending distally from the housing. The elongate shaft 604 can have a distal tip 606 configured to drive an implant, such as the pin 102, into bone. In addition, the tool 600 can include a release mechanism (not shown) coupled between the housing and the elongate shaft. For example, the release mechanism can be positioned within the housing 602. The release mechanism can have an engaged position in which the elongate shaft 604 is axially immovable (e.g., immovable along longitudinal axis L of the tool) relative to the housing 602, as well as a disengaged position in which the elongate shaft is axially movable (e.g., movable along longitudinal axis L of the tool) relative to the housing.

Further, the release mechanism can be configured to move from the engaged position to the disengaged position when a force is applied to move at least a portion of the release mechanism proximally relative to the housing 602. For example, in some embodiments the release mechanism can include a trigger element 608 extending distally from the housing 602. The trigger element 608 can be movable relative to the housing 602 such that proximal movement of the trigger element can actuate the release mechanism and cause it to move from the engaged position to the disengaged position.

In use, a surgeon or other user can insert an implant (e.g., pin 102) into a delivery cannula 202 and then insert the distal tip 606 of the medical driver tool 600 into the delivery cannula. The distal tip 606 of the elongate shaft 604 can contact a proximal end of the pin 102, and the cross-pin can be driven into bone by delivering an impacting force to a proximal end 610 of the tool 600, e.g., the proximal end of the housing 602. Due to the fact that the release mechanism is in the engaged position, the housing 602 and the elongate shaft 604 cannot be moved relative to one another and the impacting force can be transferred to the pin 102.

When the cross-pin or other implant has been driven to a predetermined depth (set by the length of the elongate shaft 604 and the length of any delivery cannula being used), a proximal end of the delivery cannula 202 can contact the trigger element 608 of the release mechanism and move the trigger element 608 proximally relative to the housing 602. This proximal force on the trigger element 608 from the delivery cannula 202 can cause the release mechanism to move to the disengaged position in which the elongate shaft 604 can move axially relative to the housing 602. Still further, in some embodiments, the release mechanism can be configured to move the elongate shaft 604 proximally relative to the housing 602 when moving from the engaged position to the disengaged position.

Figure 6B:
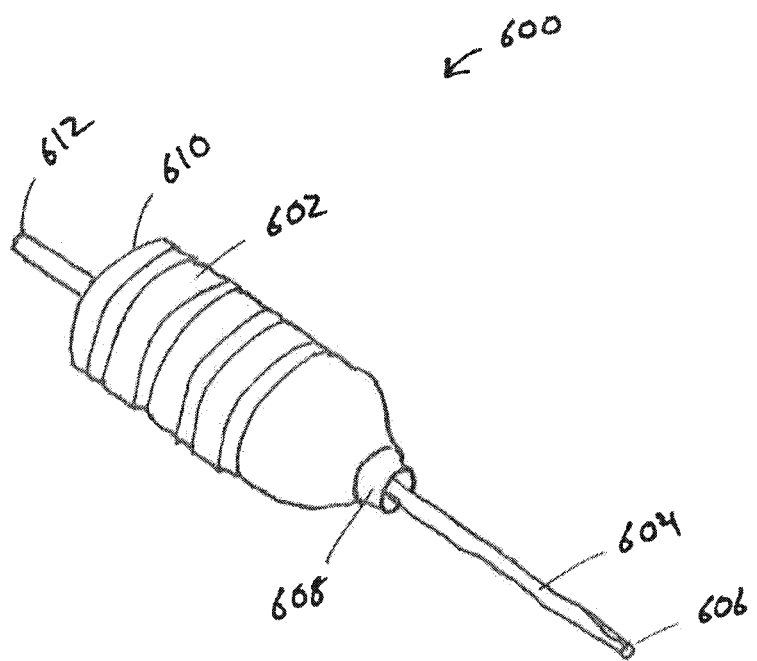
FIG. 6B is an illustration of the medical driver tool of FIG. 6A in a second configuration.

The proximal movement of the elongate shaft 604 relative to the housing 602 can result in a proximal end 612 of the elongate shaft extending proximally from the housing 602, as shown in FIG. 6B. Similar to a pop-up meat thermometer, the proximal extension of the elongate shaft 604 from the housing 602 can provide a user with a visual indication that the desired depth of insertion has been reached. Further, the proximal movement of the elongate shaft 604 relative to the housing 602 retracts the elongate shaft within the delivery cannula 202 such that its distal tip 606 no longer contacts the proximal end of the implant. Therefore, even if the user ignores the indication that the desired depth has been reached and continues to impart an impacting force, the elongate shaft 604 will be driven distally without further driving the implant into bone. In some cases, a single tap from a hammer or other impacting tool can advance a tool about 5 mm. As a result, in some embodiments the release mechanism can be configured to move the elongate shaft 604 proximally by at least 5 mm. In other embodiments, the release mechanism can be configured to move the elongate shaft proximally by a distance greater than 5 mm to provide a safety factor. The distance can be in a range of about 7 mm to about 10 mm in some embodiments, though other distances can also be used.

FIGS. 7-12 illustrate the medical driver tool 600 in more detail. As shown in the exploded view of FIG. 7, the medical driver tool includes a release mechanism 700 positioned within the housing 602 and coupled between the housing and the elongate shaft 604. The release mechanism 700 can itself include a number of components, including the trigger element 608. The release mechanism can also include a base member 702 that threadably couples to the housing 602. Also shown are a plurality of retaining balls 704 that can selectively secure the elongate shaft 604 relative to the housing 602, and a retaining ring 710.

Figure 7:
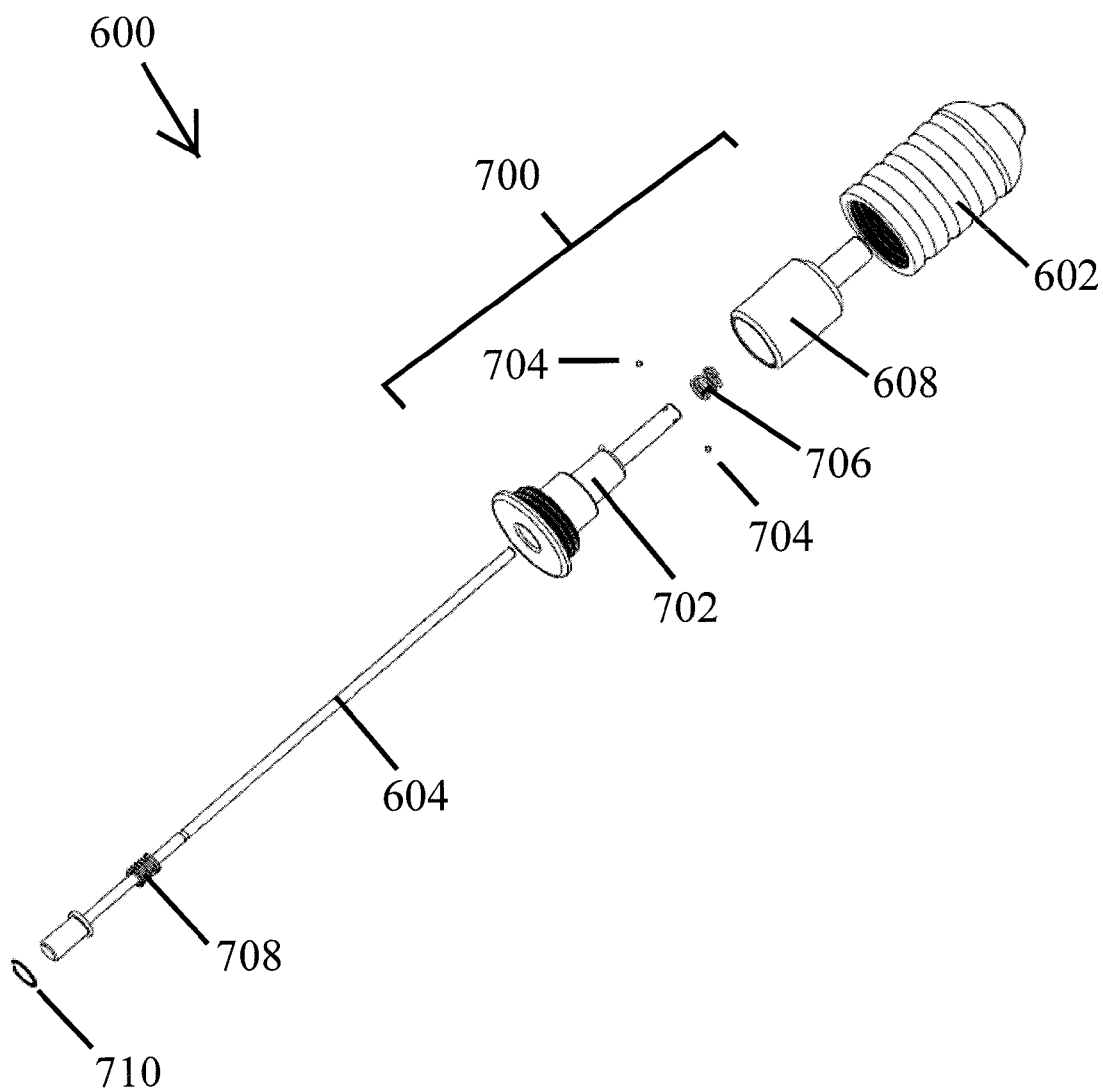
FIG. 7 is an exploded view of one embodiment of a medical driver tool.

FIG. 7 also shows a trigger element biasing member 706 that biases the trigger element in a distal direction relative to the housing 602, and an elongate shaft biasing member 708 that can cause the elongate shaft to move proximally when the release mechanism moves from the engaged position to the disengaged position. Both biasing members can be coil springs or other resilient members formed from biocompatible materials, such as stainless steel.

Figure 8:
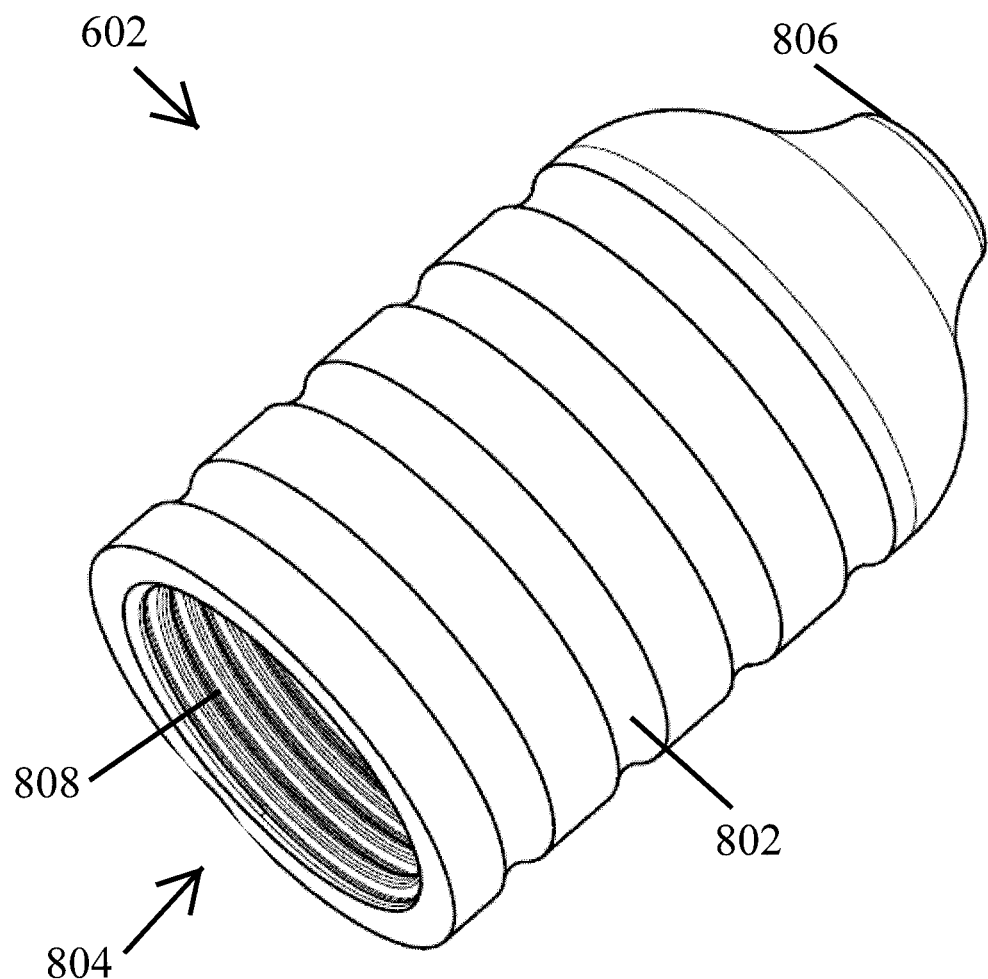
FIG. 8 is an illustration of a housing of the medical driver tool of FIG. 7.

FIG. 8 illustrates the housing 602 in more detail. The housing 602 can have a generally cylindrical shape with an outer surface 802 and an inner lumen 804 extending therethrough. The outer surface 802 can include one or more grooves, knurled portions, flat portions, raised features, indented features, or any other feature known in the art to enhance a user's grip on the medical driver tool 600. Typically, a surgeon or other user will hold the tool 600 in one hand by gripping the outer surface 802 of the housing 602 and provide an impacting force to the proximal end of the tool using a hammer held in their other hand.

At a proximal end of the housing 602, a surface of the inner lumen can include threads 808 formed thereon. The threads can extend along any portion of the inner lumen 804 and can be configured to mate with complementary threads formed on the base member 702. In some embodiments, the threads can extend at least about 0.9 cm from the proximal end of the housing. By threadably coupling the base member 702 and the housing 602, the base member can be rigidly anchored to the housing 602 and provide a secure base that can be used to load the biasing members 706, 708.

The housing 602 can also include a tapered distal end 806, and the lumen 804 can extend through a smaller opening formed in the distal end 806 (not shown, see FIG. 6A). This smaller opening can be configured to accommodate the elongate shaft 604 and distal end of the trigger element 608, for example.

The housing 602 can have a variety of sizes, but in some embodiments the housing 602 can have an overall length in a range of about 4 cm to about 7 cm. In certain embodiments, the overall length of the housing 602 can be about 5.5 cm. An outer diameter of the housing 602 can be in a range of about 2 cm to about 3 cm. In some embodiments, the outer diameter of the housing 602 can be about 2.5 cm. A diameter of the inner lumen 804 extending through the housing 602 can be in a range of about 1 cm to about 3 cm at its widest point and, in some embodiments, the diameter of the inner lumen can be about 2 cm at its widest point. At the tapered distal end 806, a diameter of the inner lumen can be in a range of about 0.5 cm to about 1.5 cm and, in some embodiments, a diameter of the inner lumen at the tapered distal end 806 can be about 0.9 cm.

Figure 9:
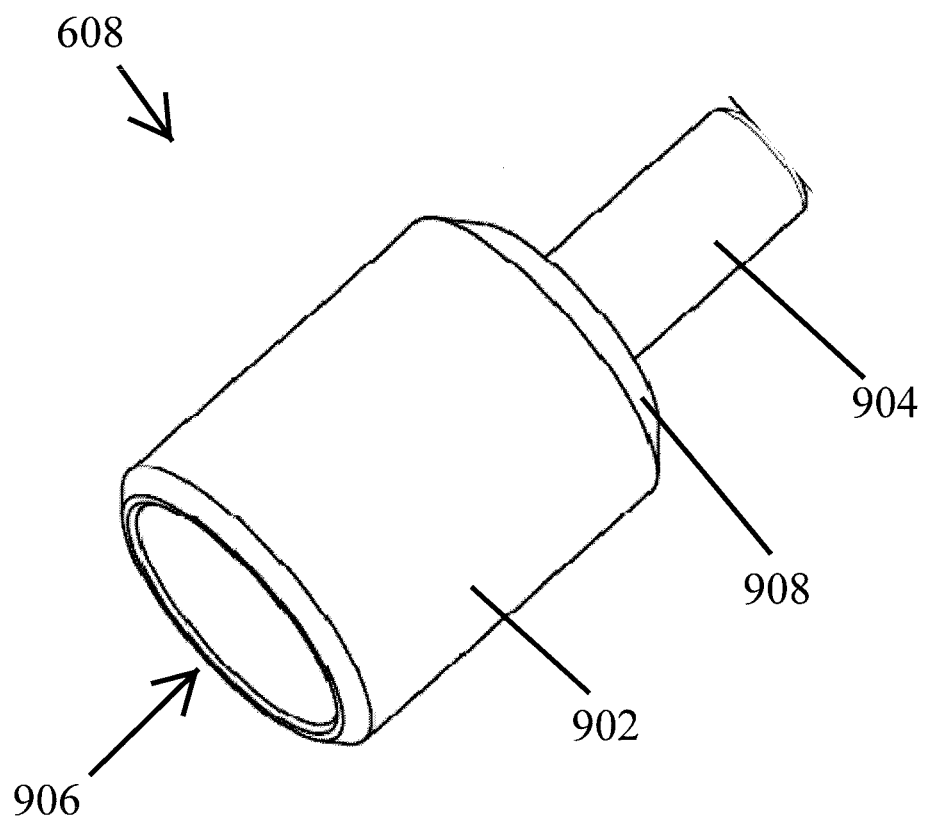
FIG. 9 is an illustration of a trigger element of the medical driver tool of FIG. 7.

FIG. 9 illustrates the trigger element 608 of the release mechanism 700 in more detail. The trigger element 608 can include a proximal cylindrical portion 902 and a distal cylindrical portion 904 having different diameters, as well as an inner lumen 906 extending through both portions. The diameter of the proximal cylindrical portion 902 can be sized to fit within a proximal portion of the inner lumen 804 of the housing 602, and the distal cylindrical portion 904 can be sized to pass through the opening in the tapered distal end 806 of the housing, as shown in FIG. 6A. Further, a distal outer edge 908 of the proximal cylindrical portion 902 can be angled such that it matches a profile of the surface of the inner lumen 804 of the housing 602 near its tapered distal end 806. Still further, an inner surface of the distal cylindrical portion 904 can include an annular recess (not shown, see 1202 of FIG. 12) formed therein that can be configured to provide clearance for the plurality of retaining balls 704, as discussed in more detail below.

While the illustrated embodiment includes a distal cylindrical portion 904 that can be well suited to contacting a cylindrical delivery cannula 202, in other embodiments a distal portion of the trigger element can have any of a variety of other shapes. For example, in an embodiment in which a delivery cannula is not used and the trigger element is configured to contact a patient's skin surface directly, a distal portion of the trigger element can have an alternative shape. An exemplary alternative shape can include, for example, a flange formed at a distal end of the trigger element to provide a larger surface area to contact the patient's skin. The flange can aid in counteracting compression of the soft skin surface that can delay application of a sufficient proximal force to the trigger element. In still other embodiments, a distal portion of the trigger element can include an arm extending laterally from the tool and configured to contact some other surgical component (e.g., a table, etc.) to indicate a predetermined insertion depth has been reached. All of these variations are considered within the scope of the invention.

Figure 10:
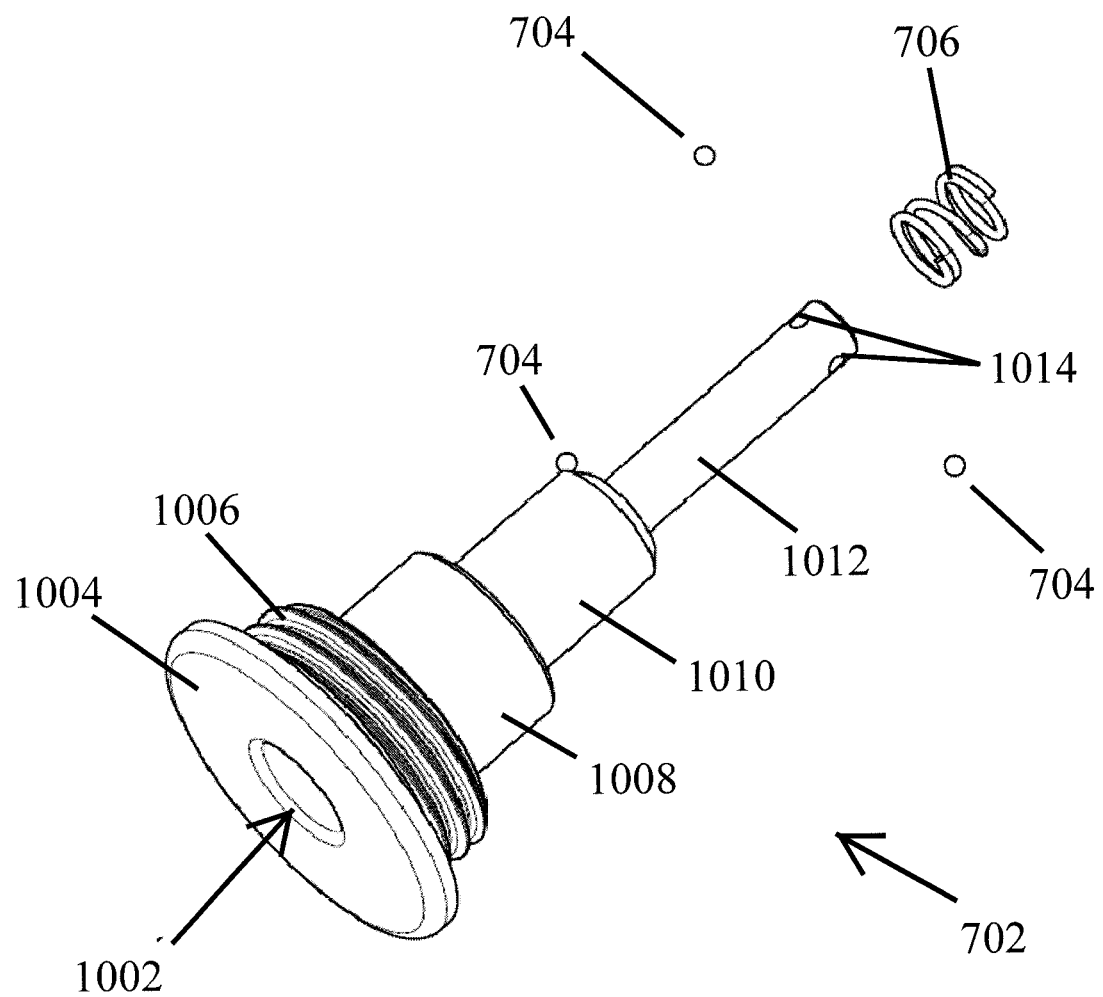
FIG. 10 is an illustration of a base member, retaining balls, and biasing member of the medical driver tool of FIG. 7.

Returning to the illustrated embodiment, the base member 702, retaining balls 704, and trigger element biasing member 706 are shown in FIG. 10. The base member 702 can have an elongate cylindrical profile with an inner lumen 1002 extending therethrough and one or more sections having different diameters. For example, the base member 702 can include a proximal flange 1004 having an outer diameter substantially equal to an outer diameter of the housing 602. A coupling portion 1006 having a reduced diameter relative to the flange can extend proximally from the flange 1004. The coupling portion 1006 can have threads formed on an outer surface thereof that are configured to mate with the threads 808 of the inner lumen 804 of the housing 602.

A first cylindrical portion 1008 can extend distally from the coupling portion 1006 and can have a diameter sized to fit within the inner lumen 906 of the proximal portion 902 of the trigger element 608. A second cylindrical portion 1010 can extend distally from the first cylindrical portion 1008, and a distal cylindrical portion 1012 can extend distally from the second cylindrical portion 1010. The distal cylindrical portion 1012 can be sized to fit within the inner lumen 906 extending through the distal portion 904 of the trigger element 608.

The distal cylindrical portion 1012 can also include a plurality of boreholes 1014 formed around a circumference thereof at its distal end. The boreholes 1014 can be evenly spaced around the circumference of the distal cylindrical portion 1012 and can be sized to receive a retaining ball 704. Though the illustrated embodiment shows three retaining balls 704, any other number can be used depending on their size. For example, in an alternative embodiment, six retaining balls 704 can be included in a medical driver tool.

The retaining balls 704 can be ball bearings or other smooth spherical balls made from a biocompatible material. The retaining balls can have a variety of sizes, and can be sized to correspond with a detent formed in the elongate shaft 604 such that the retaining balls can sufficiently restrain the elongate shaft from moving axially when the retaining balls are pressed into the detent.

Figure 12:
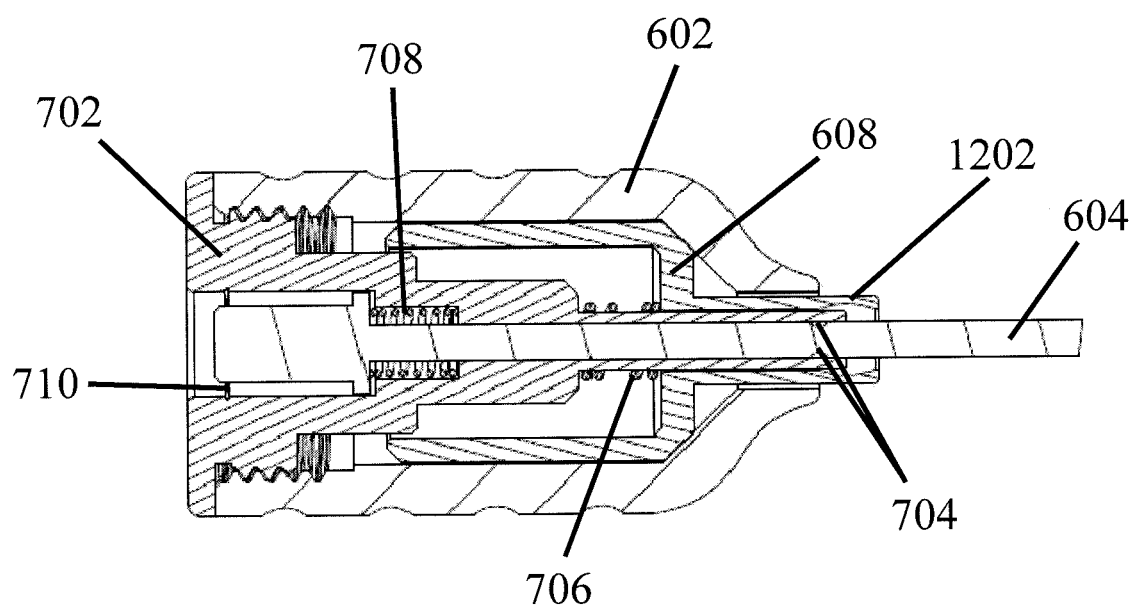
FIG. 12 is a cross-sectional view of the medical driver tool of FIG. 7.

As mentioned above, the trigger element biasing member 706 can be a spring or other resilient member formed from a biocompatible material. In the illustrated embodiment, the trigger element biasing member 706 is a coil spring sized to slide over the distal cylindrical portion 1012 of the base member 702 without being able to pass over the second cylindrical portion 1010. In addition, the trigger element biasing member 706 can be sized such that it cannot be received within the inner lumen 906 extending through the distal portion 904 of the trigger element 608. As a result, the trigger element biasing member 706 can be restrained between the second cylindrical portion 1010 of the base member 702 and the distal portion 904 of the trigger element 608, as shown in FIG. 12.

Figure 11:
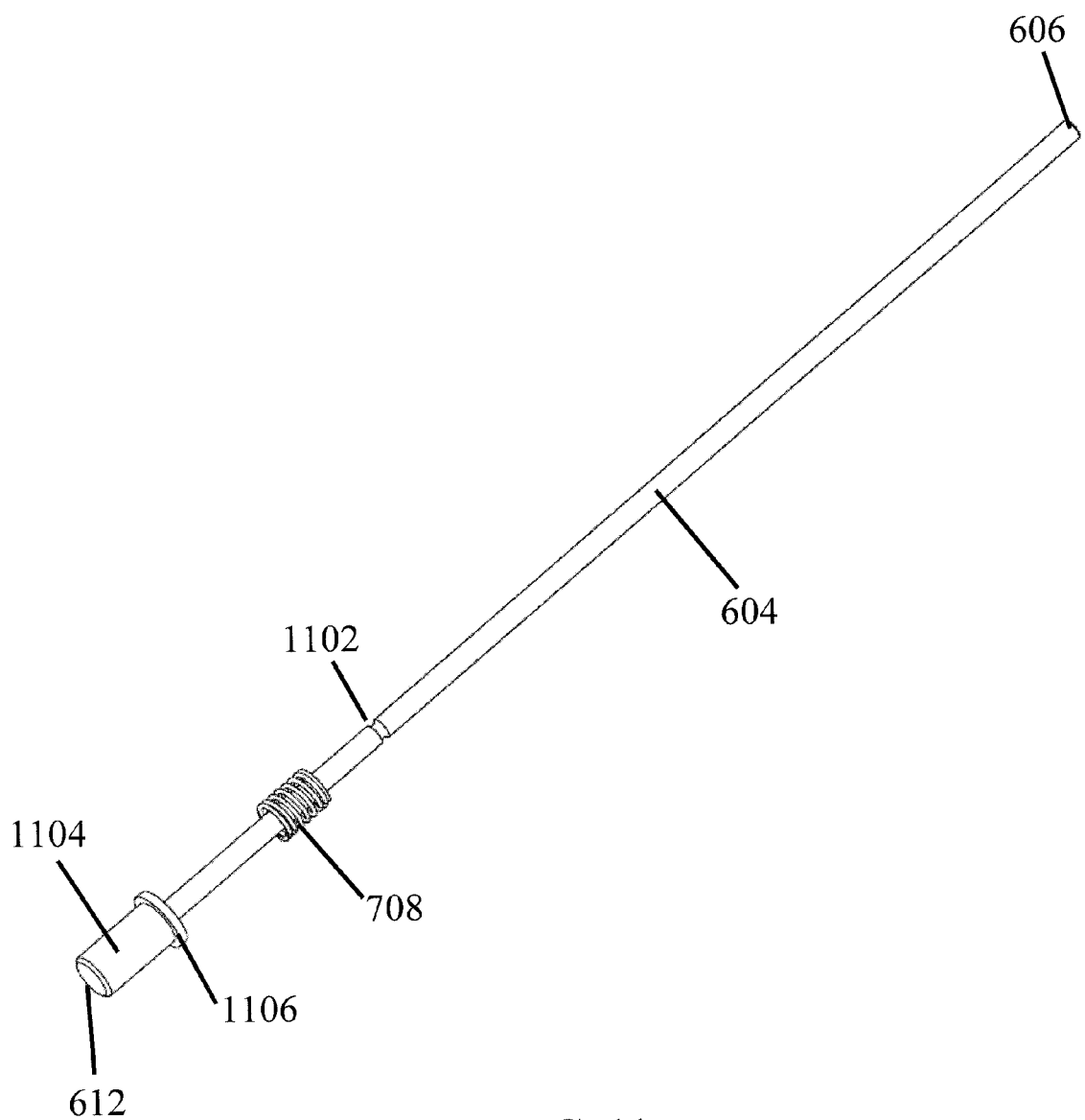
FIG. 11 is an illustration of an elongate shaft and biasing member of the medical driver tool of FIG. 7.

FIG. 11 illustrates the elongate shaft 604 and elongate shaft biasing member 708. As mentioned above, the elongate shaft 604 can have a distal tip 606 and a proximal end 612. The elongate shaft can also include one or more detents formed on an outer surface thereof. In some embodiments, a plurality of detents can be formed in the outer surface and spaced about the circumference of the elongate shaft 604 to line up with the boreholes 1014 formed in the base member 702. In other embodiments, however, a single detent or groove 1102 can be formed running along the entire circumference of the elongate shaft 604. In such a configuration, the rotational orientation of the elongate shaft 604 does not matter when assembling the device, and the elongate shaft 604 can be rotated relative to the housing 602 even when the release mechanism is in the engaged position and the elongate shaft is not axially movable relative to the housing.

Similar to the trigger element biasing member 706, the elongate shaft biasing member 708 can be a spring or other resilient member formed from a biocompatible material. In the illustrated embodiment, a coil spring is sized so as to slide over the elongate shaft 604 along its length until reaching an enlarged diameter portion 1104 at the proximal end of the shaft. As a result of this configuration, the elongate shaft biasing member 708 can be compressed between the enlarged diameter portion 1104 of the elongate shaft and a portion of an inner lumen of the base member 702. As a result of this compression, the elongate shaft biasing member 708 can move the elongate shaft proximally when the release mechanism 700 is actuated to move from the engaged position to the disengaged position. The enlarged diameter portion 1104 can also include a flange 1106 formed at a distal end thereof, and the flange can be configured to abut against the retaining ring 710 to prevent the elongate shaft 604 from moving too far proximally in response to a force from the elongate shaft biasing member 708.

The length of the elongate shaft 604 can vary depending on the size of the medical driver tool 600 and the desired depth of insertion of an implant to be used with the device. In some embodiments, however, the elongate shaft 604 can have an overall length in a range of about 15 cm to about 25 cm. In certain embodiments, the overall length of the elongate shaft can be about 19 cm. The elongate shaft 604 can also have a variety of diameters. In some embodiments, the elongate shaft can have a diameter in a range of about 2 mm to about 4 mm. In one embodiment, for example, the elongate shaft 604 can have a diameter of about 3 mm along its length, except for the enlarged diameter portion 1104 that can have a diameter in a range of about 4 mm to about 6 mm.

In any embodiment, the elongate shaft and other components can be sized to fit together as shown in the cross-sectional illustration of FIG. 12. Illustrated with the release mechanism in the engaged position, the figure shows the elongate shaft 604 extending through the base member 702, trigger element 608, and housing 602. The base member 702 is threadably coupled to and positioned within the inner lumen of the housing 602 and extends through the inner lumen of the trigger element 608. The trigger element 608 is also disposed within the inner lumen of the housing 602 near its tapered distal end, and a distal end of the trigger element extends from the distal end of the housing. Further, the trigger element biasing member 706 is compressed between the base member 702 and the trigger element 608, thereby biasing the trigger element distally relative to the housing 602. At its illustrated distal-most position, the angled outer edge 908 of the trigger element 608 abuts against the angled surface of the inner lumen of the housing 602. In addition, the elongate shaft biasing member 708 is compressed between the base member 702 and the elongate shaft 604, thereby biasing the elongate shaft proximally relative to the housing.

The elongate shaft is restrained from moving proximally by the plurality of retaining balls 704 that are pressed into the detent 1102 formed in the outer surface of the elongate shaft 604. In particular, the retaining balls 704 are positioned within the boreholes 1014 formed in the base member 702 and are pressed into the detent 1102 of the elongate shaft 604 by the inner sidewalls of the distal portion 904 of the trigger element 608. Also visible in cross-section is the annular recess 1202 formed in the inner sidewall of the trigger element 608. In the engaged position, the annular recess 1202 is positioned distally of the boreholes 1014 formed in the base member 702.

In the illustrated configuration (i.e., the engaged position of the release mechanism), the elongate shaft 604 is axially immovable relative to the housing 602. That is, the shaft cannot move proximally and distally relative to the housing, though it can be rotated. Accordingly, an impact force delivered to the proximal end of the tool (e.g., by striking the base member 702 with a hammer) can be transferred through the rigid structure to the implant (e.g., pin 102) that is in contact with the distal tip 606 of the elongate shaft 604.

To move the release mechanism from the engaged position to the disengaged position, a proximal force can be applied to the distal end of the trigger element 608 (e.g., by a proximal end of a delivery cannula as the correct implantation depth is reached). If the proximal force is sufficiently strong, it will overcome the bias force of the trigger element biasing member 706 and the trigger element 608 will begin to move proximally relative to the housing 602. As it does so, the annular recess 1202 of the trigger element 608 can become aligned with the boreholes 1014 formed in the base member 702, thereby allowing the retaining balls 704 to move out of the detent 1102 toward the annular recess 1202 (i.e., the retaining balls 704 can move radially away from the elongate shaft 604). As the retaining balls move out of the detent 1102, the elongate shaft 604 becomes free to move axially relative to the housing 602. In some embodiments, moving the trigger element 608 proximally by about 1 mm can align the annular recess 1202 with the boreholes 1014 and allow the release mechanism to move from the engaged position to the disengaged position.

Once the elongate shaft 604 becomes free to move axially relative to the housing 602, the biasing force of the elongate shaft biasing member 708 can urge the elongate shaft proximally. This can proximal movement of the elongate shaft 604 can cause the proximal end of the shaft to extend from the proximal end of the base member 702. Proximal movement of the elongate shaft 604 can be halted when the flange 1106 abuts against the retaining ring 710.

The proximal extension of the shaft can serve as a visual indicator to a user that the proper depth of insertion has been reached. In addition, the proximal movement of the elongate shaft 604 brings the distal tip 606 of the shaft out of contact with the implant (e.g., pin 102). Accordingly, even if the user ignores the indication and delivers a subsequent impacting force to the tool 600, the implant will not be driven farther into bone. As mentioned above, the release mechanism of the medical driver tool can be configured to move the elongate shaft proximally by a variety of distances upon moving into the disengaged position. In some embodiments, the elongate shaft can be moved proximally by a distance sufficient to prevent an implant from being driven farther into bone by the delivery of a single impacting force from a user. In some embodiments, the distance can be in a range of about 7 mm to about 10 mm, though any of a variety of other distances can be utilized as well, as discussed above.

Choosing the spring constant or stiffness for the trigger element and elongate shaft biasing members 706, 708 can be important to prevent unintended operation of the tool 600. For example, if the spring constant for the trigger element biasing member 706 is too weak, delivering an impacting force to the tool 600 can cause oscillations of the trigger element 608 that might inadvertently actuate the release mechanism and free the elongate shaft 604. Conversely, if the biasing member 706 is too stiff, it may never actuate despite abutting against the proximal end of a delivery cannula, patient skin surface, etc. In some embodiments, a spring constant of the trigger element biasing member 706 can be in a range of about 0.5 N/mm to about 1.5 N/mm. In one exemplary embodiment, the spring constant of the trigger element biasing member 706 can be about 1.2 N/mm.

With respect to the elongate shaft biasing member 708, choosing a spring constant that is too strong can risk moving the elongate shaft 604 proximally with too much force when the release mechanism is actuated and moves to the disengaged position. If the elongate shaft is moved with enough force, the press-fit retaining ring 710 could be dislodged. In certain embodiments, the spring constant of the elongate shaft biasing member 708 can be in a range of about 0.2 N/mm to about 0.7 N/mm.

The release mechanism 700 of the medical driver tool 600 can repeatedly be moved between the engaged position and the disengaged position, thereby allowing the driver tool to be reused. To move the release mechanism back to the engaged position after it has been actuated by a proximal force applied to the trigger element 608, a user can release the proximal force on trigger element 608 and push the elongate shaft 604 distally relative to the housing 602. When the detent 1102 of the elongate shaft 604 is aligned with the boreholes 1014 formed in the base member, the biasing force from the trigger element biasing member 706 will urge the trigger element distally and the sidewalls of the trigger element inner lumen will in turn urge the retaining balls 704 to move into the detent (i.e., move the retaining balls radially toward the elongate shaft). The release mechanism 700 will then be reset in the engaged position, as shown in FIG. 12.

Figure 13:
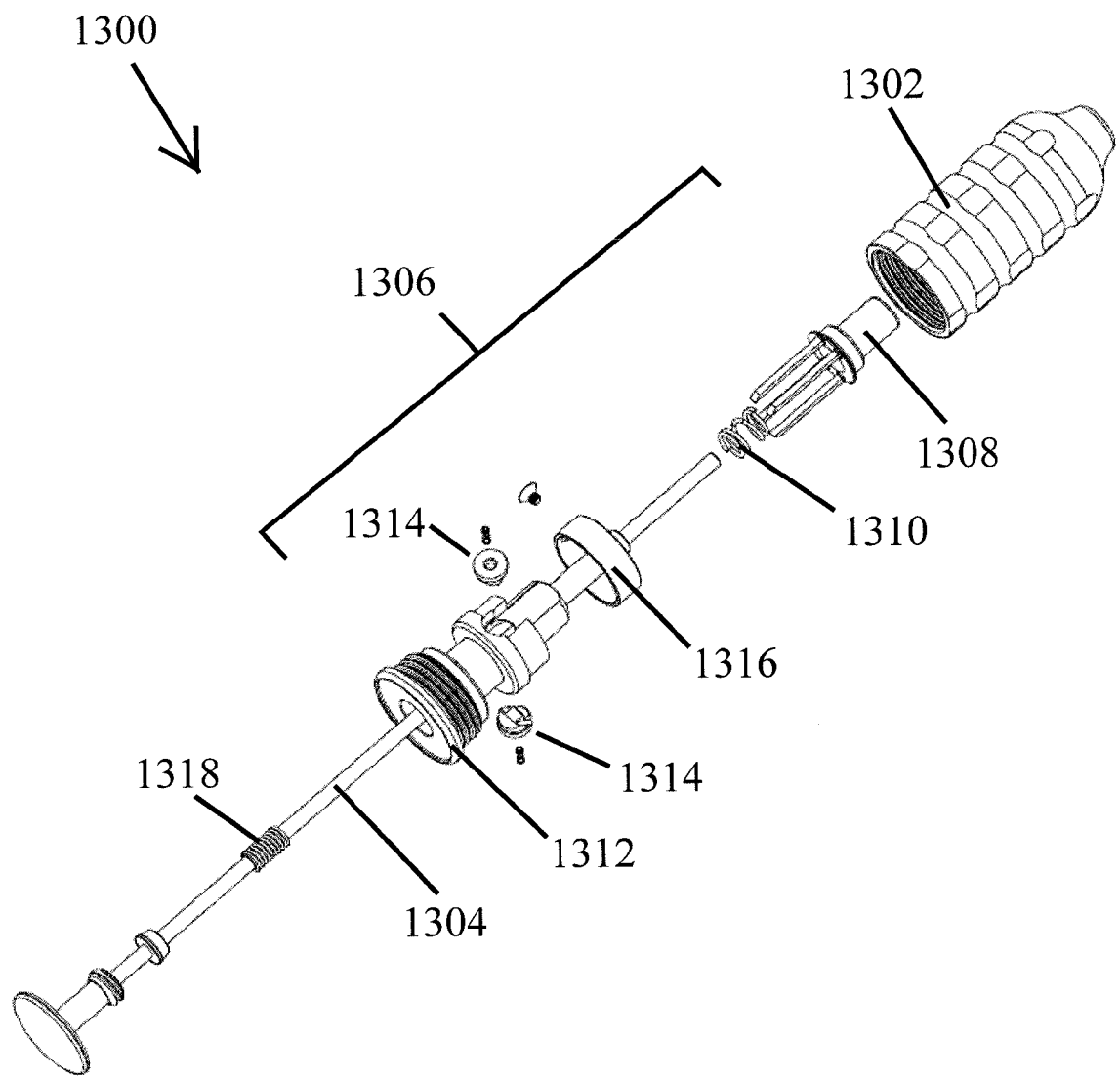
FIG. 13 is an exploded view of an alternative embodiment of a medical driver tool.

FIG. 13 illustrates another embodiment of a medical driver tool 1300 that is similar to the driver tool 600 discussed above. The medical driver tool 1300 includes a housing 1302 that is similar to the housing 602, and an elongate shaft 1304 that is similar to the elongate shaft 604. Accordingly, the description set forth above with respect to those components applies equally to driver tool 1300. In this embodiment, a release mechanism 1306 of the medical driver tool 1300 utilizes a plurality of biased retaining pins 1314 that interface with a shoulder formed on the elongate shaft 1304, rather than retaining balls 704 that interface with a detent 1102. The medical driver tool 1300 also includes an alternative embodiment of a trigger element 1308 and base member 1312. The release mechanism 1306 also includes a retaining cap 1316 to restrain the biased retaining pins 1314 relative to the base member 1312. Finally, the tool 1300 includes a trigger element biasing member 1310 and an elongate shaft biasing member 1318 that are similar to the biasing members 706 and 708 described above.

Figure 14:
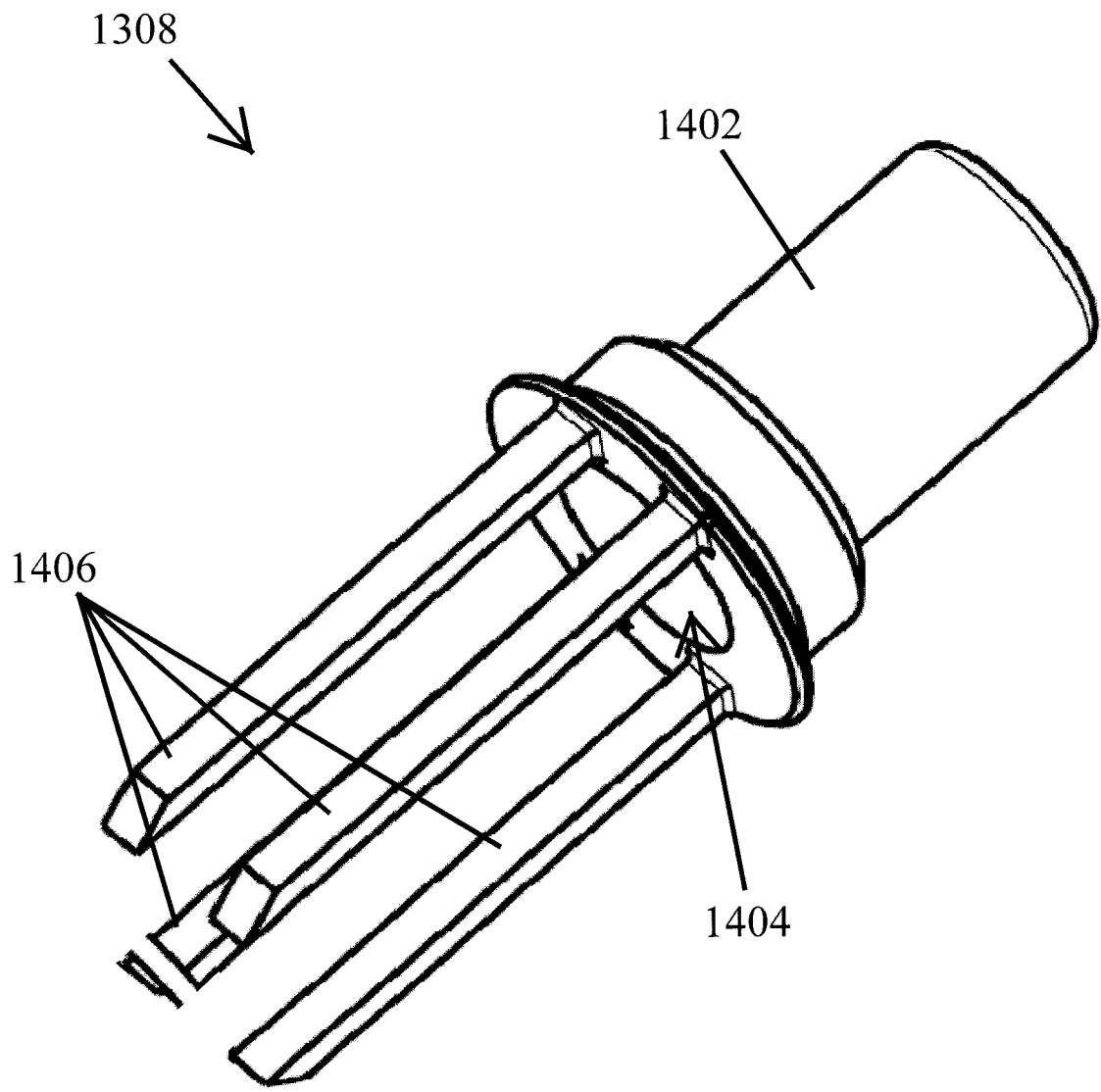
FIG. 14 is an illustration of a trigger element of the medical driver tool of FIG. 13.

FIG. 14 illustrates the trigger element 1308 in greater detail. The illustrated trigger element 1308 includes a distal cylindrical portion 1402 having an inner lumen 1404 extending therethrough. This portion can be similar to the distal cylindrical portion 904 of the trigger element 608, or in other embodiments it can have any of the alternative shapes described above with respect to the trigger element 608. A plurality of arms 1406 can extend proximally from the distal cylindrical portion 904 and can be configured to interface with the plurality of biased retaining pins 1314. In particular, the plurality of arms 1406 can be arranged into sets of two that are each configured to contact one of the plurality of biased retaining pins 1314. As shown in FIG. 14, two such sets are spaced evenly around the circumference of the trigger element 608.

The plurality of arms 1406 can have a variety of shapes and sizes but, in some embodiments, each arm can have a length of about 2 cm. In the illustrated embodiment, each arm has a square cross section, though other shapes are also possible, including, for example, circular, triangular, hexagonal, etc. In some embodiments, a cross-sectional dimension of each arm can be about 1.5 mm. In addition, a distal end of each arm can be angled so as to smoothly interface with an angled portion of the biased retaining pin 1314, as described below. In some embodiments, the distal end of each arm can slope away from the elongate shaft from the distal end of the arm at about 45°.

Figure 15:
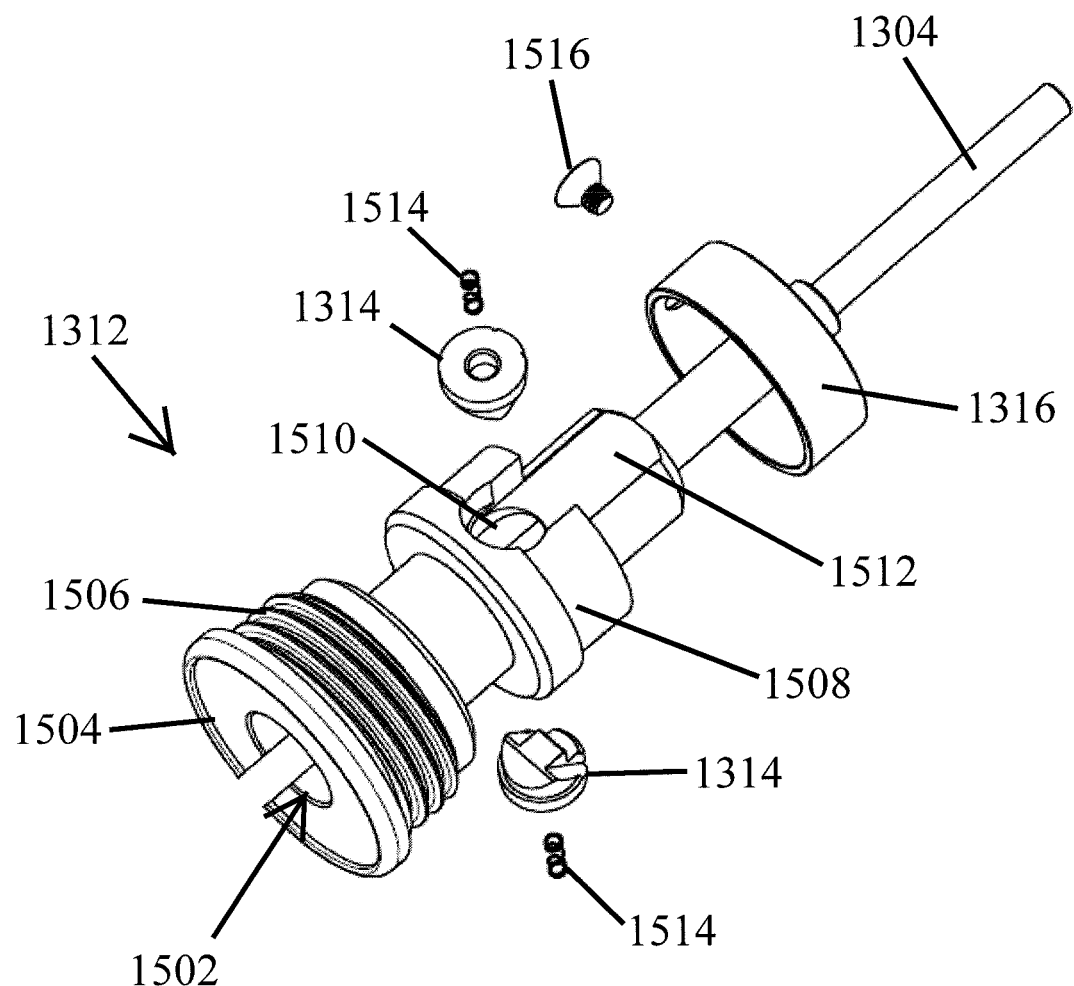
FIG. 15 is an illustration of a base member, biased retaining pins, and retaining cap of the medical driver tool of FIG. 13.

FIG. 15 illustrates the base member 1312, biased retaining pins 1314, and retaining cap 1316. The base member 1312 can have a similar elongate generally cylindrical profile as the base member 702, and can include an inner lumen 1502 extending therethrough. Also similar to the base member 702, the proximal portion of the base member 1312 can include a proximal flange 1504 and a threaded coupling potion 1506 extending distally therefrom. An enlarged diameter portion 1508 can be positioned along a length of the base member 1312 and it can include a plurality of boreholes 1510 formed therein and spaced about the circumference of the base member. In the illustrated embodiment, two opposed boreholes 1510 are included, though only one is visible in FIG. 15. The boreholes 1510 extend through the sidewall of the base member 1312 into the inner lumen 1502. Each borehole 1510 can be sized to receive a biased retaining pin 1314.

The outer surface of the base member 1312 can include a plurality of flattened portions 1512 (only one shown) extending distally from the boreholes 1510. Further, each flatted portion 1512 can be aligned with one of the plurality of boreholes 1510, as shown in FIG. 15. The flattened portions 1512 can provide a surface on which the arms 1406 of the trigger element 1308 can slide, as described below.

A retaining pin 1314 can be seated within each borehole 1510 and a retaining cap 1316 can be configured to slide over the enlarged diameter portion 1508 of the base member 1312 to prevent the retaining pins from falling out of the boreholes. Further, a biasing member 1514 can be placed between each retaining pin 1314 and the retaining cap 1316 to bias the retaining pins toward the inner lumen of the base member 1312. The position of the retaining cap 1316 can be secured with a set screw 1516 configured to be threaded into a bore (not shown) formed in the enlarged diameter portion 1508 of the base member 1312.

The base member 1312 can have any of a variety of sizes but, in some embodiments, the base member 1312 can have an overall length of about 6 cm a maximum outer diameter of about 2.5 cm. The enlarged diameter portion 1508, for example, can have an outer diameter of about 1.8 cm, and each borehole 1510 can have a diameter of about 6.6 mm.

Figure 16A:
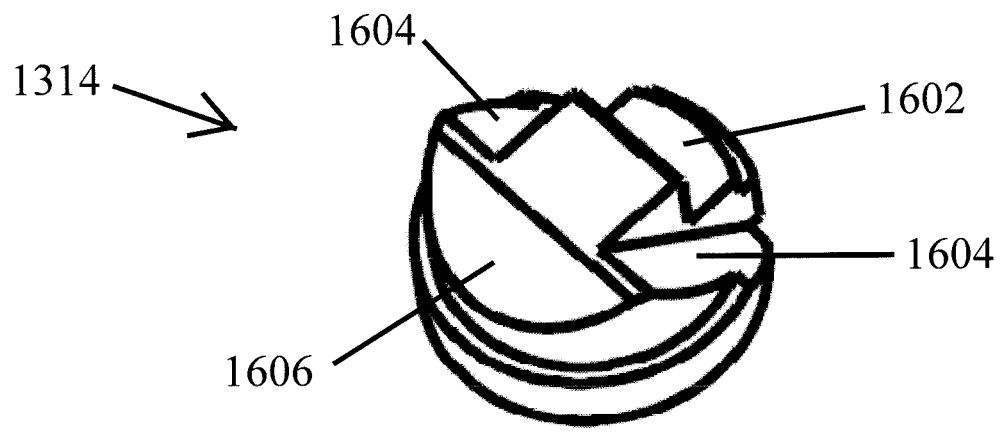
FIG. 16A is a top-isometric view of a retaining pin of the medical driver tool of FIG. 13.
Figure 16B:
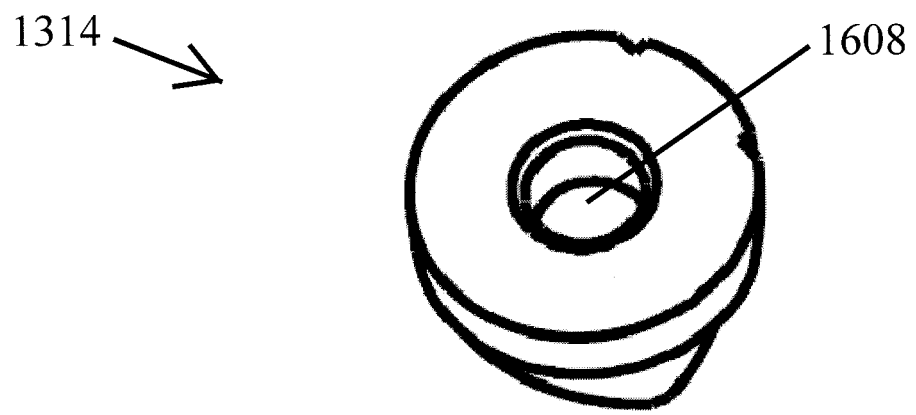
FIG. 16B is a bottom-isometric view of a retaining pin of the medical driver tool of FIG. 13.

A retaining pin 1314 is illustrated in FIGS. 16A and 16B. The retaining pin 1314 can have a generally cylindrical shape with one or more features formed in its outer surfaces. In some embodiments, an outer diameter of the retaining pin 1314 can be about 7 mm and a height of the retaining pin can be about 3.8 mm. An upper surface of the pin 1314 can include an "L" shaped or perpendicular cutout 1602 configured to face toward a distal end of the medical driver tool 1300 and engage a shoulder 1702 (see FIG. 17) formed on the elongate shaft 1304 so as to prevent proximal movement of the elongate shaft 1304 relative to the housing 1302. The retaining pin 1314 can also include distally sloped portions 1604 on either side of the perpendicular cutout 1602. The distally sloped portions 1604 can be angled to complement the angled distal ends of the arms 1406 of the trigger element 1308. In the illustrated embodiment, for example, the distally sloped portions 1604 can be angled at about 45° and can slope away from the elongate shaft 1304 toward the distal end of the tool 1300. The slope of these portions of the retaining pin 1314 can allow proximal movement of the trigger element 1308 to move the retaining pin against the biasing member 1514, as described in more detail below.

In addition, a proximally sloped portion 1606 can be positioned opposite the distally sloped portions 1604 and the perpendicular cutout 1602. The proximally sloped portion can slope away from the elongate shaft 1304 toward the proximal end of the tool 1300 and can allow the release mechanism 1306 to be reset into the engaged position for subsequent reuse after actuation. In some embodiments, the slope of the portion 1606 can be about 30°.

As shown in FIG. 16B, a bottom surface of the pin 1314 can be substantially flat and include a bore 1608 formed therein to receive one end of the biasing member 1514 (e.g., a coil spring). An opposing end of the biasing member 1514 can abut against an inner surface of the retaining cap 1316 to allow the biasing member 1514 to urge the retaining pin 1314 toward the elongate shaft.

Figure 17:
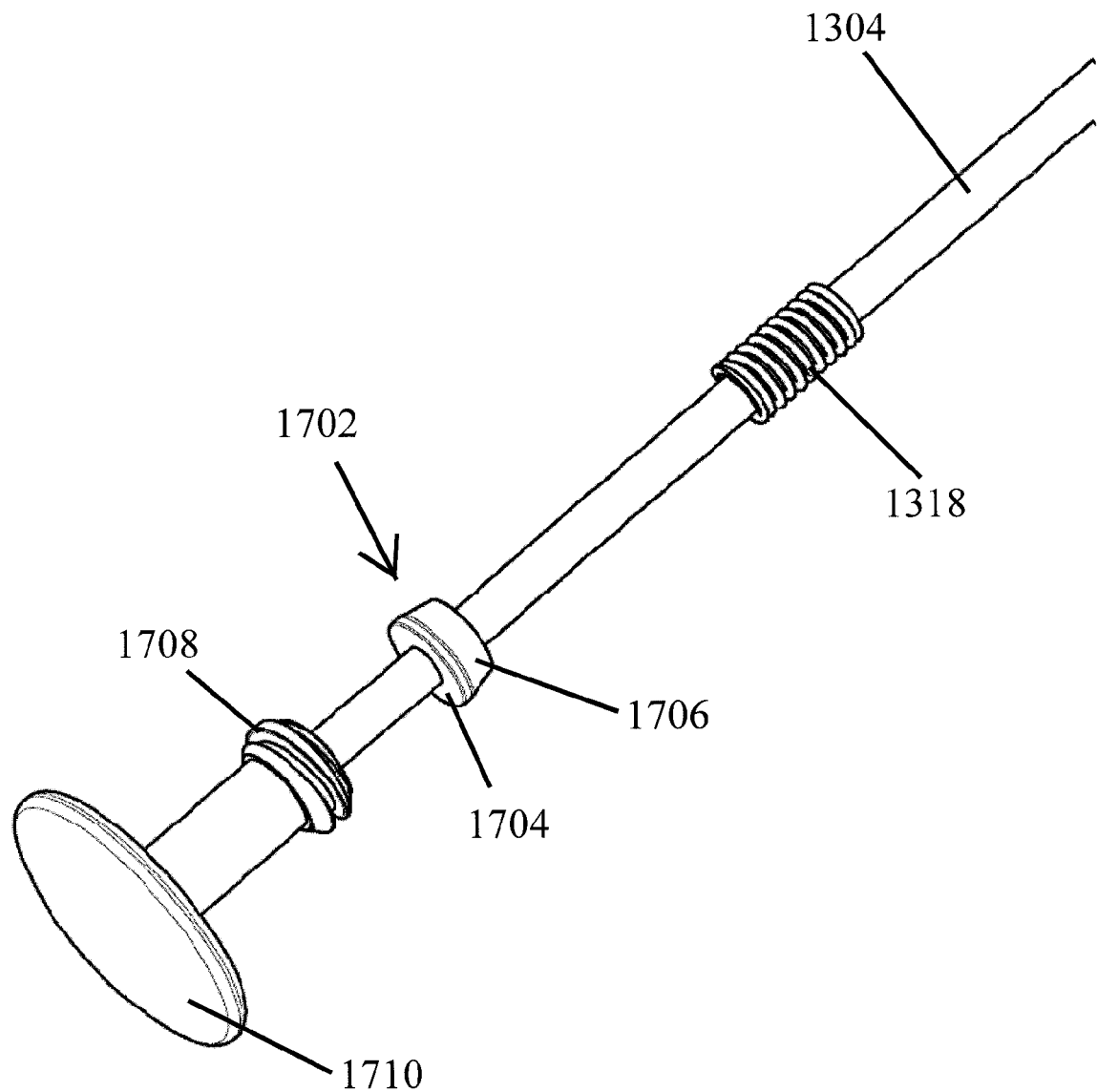
FIG. 17 is an illustration of an elongate shaft and biasing member of the medical driver tool of FIG. 13.

FIG. 17 illustrates a proximal portion of the elongate shaft 1304. The elongate shaft can include a shoulder 1702 formed thereon, and the shoulder can include a proximal-facing perpendicular face 1704 and a distal-facing tapered face 1706. The elongate shaft 1304 can also include a threaded portion 1708 that can be configured to thread into an inner lumen of a base member, as described in more detail below. Finally, the elongate shaft 1304 can include a proximal flange 1710 formed at a proximal end thereof. The proximal flange 1710 can increase the surface area of the shaft available for striking with an impaction tool, such as a hammer. In addition, the flange 1710 can be configured to sit within a recess formed in the proximal flange 1504 of the base member 1312 when the release mechanism is in the engaged position. Also shown in the figure is the elongate shaft biasing member 1318 that is similar to the biasing member 708.

Figure 18:
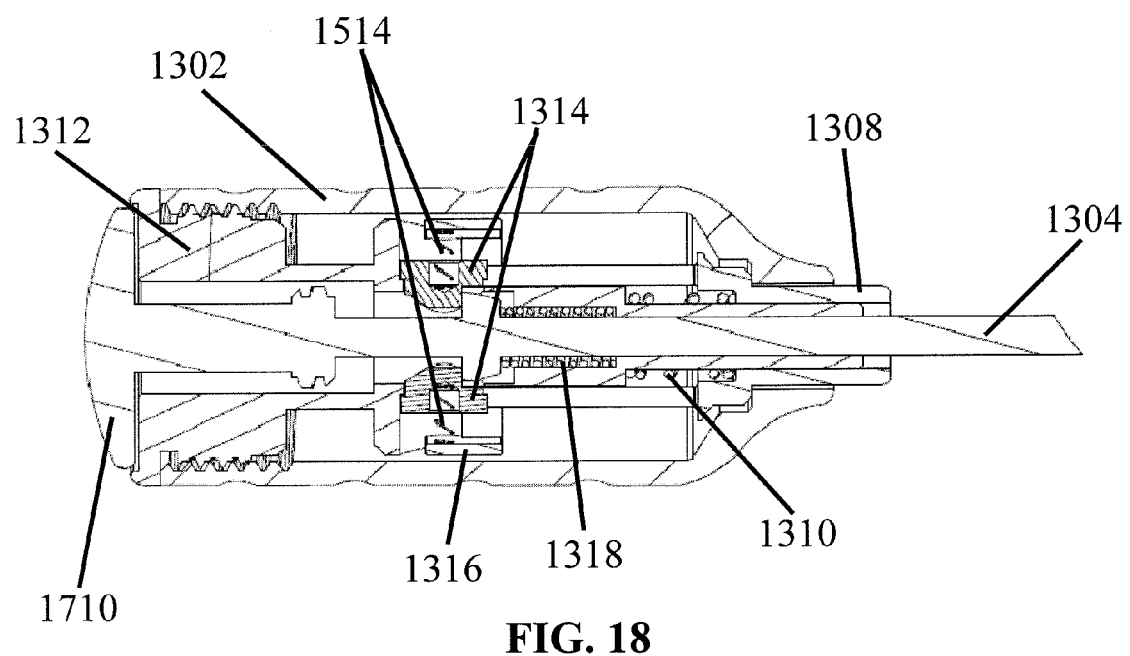
FIG. 18 is a cross-sectional view of the medical driver tool of FIG. 13.

FIG. 18 illustrates the assembled medical driver tool 1300 in cross-section. As shown in the figure, the release mechanism is in the engaged position and the elongate shaft 1304 is axially immovable relative to the housing 1302. Similar to the tool 600 described above, the trigger element 1308 is disposed within the inner lumen of the housing 1302 at the tapered distal end thereof such that a distal end of the trigger element 1308 extends from the housing 1302. The base member 1312 is threadably coupled to the housing 1302 such that a distal end of the base member extends through the inner lumen of the trigger element 1308. Furthermore, the trigger element 1308 is oriented such that each set of arms 1406 extends over one of the flattened portions 1512 of the base member 1312 toward one of the plurality of boreholes 1510 formed in the base member. A retaining pin 1314 is seated within each of the two opposed boreholes 1510 such that the bore 1608 formed therein points away from the inner lumen of the base member 1312. The retaining cap 1316 is secured over the retaining pins 1314, and a biasing member 1514 is disposed between the retaining cap and the bore 1608 formed in each retaining pin. Finally, the elongate shaft 1304 extends through the inner lumens of the base member 1312, trigger element 1308, and housing 1302.

In the illustrated engaged position, the perpendicular cutout of each retaining pin 1314 abuts against the perpendicular face 1704 of the shoulder 1702 formed on the elongate shaft 1304. This interface resists the biasing force of the elongate shaft biasing member 1318, which urges the elongate shaft in the proximal direction relative to the housing 1302, and ensures that the elongate shaft cannot move proximally relative to the housing 1302. In addition, the flange 1710 formed at the proximal end of the elongate shaft 1304 can abut against the proximal end of the base member 1312, thereby preventing the elongate shaft from moving distally relative to the housing 1302. Accordingly, any impact force delivered to the proximal end of the tool 1300 can be efficiently transferred to an implant (e.g., pin 102) in contact with a distal end of the elongate shaft 1304.

As the implant (e.g., pin 102) is driven to a predetermined depth by repeated delivery of an impacting force on the proximal end of the medical driver tool 1300, the proximal end of a delivery cannula or, in some embodiments, a patient's skin surface or other element, can contact the portion of the trigger element 1308 extending distally from the housing 1302 and exert a proximal force thereon. If the force is sufficiently large, the biasing force of the trigger element biasing member 1310 can be overcome and the trigger element will begin moving proximally relative to the housing 1302. As the trigger element moves proximally, the arms 1406 can slide over the flattened portions 1512 of the base member 1312 and the sloped distal ends of the arms can contact the distally sloped portions 1604 of the retaining pins 1314. With continued proximal movement, the arms 1406 can overcome the biasing force of the biasing members 1514 and move the retaining pins 1314 away from the elongate shaft (i.e., radially away from the shaft). In some embodiments, moving the trigger element 1308 proximally by about 1 mm can move the retaining pins 1314 far enough to clear the shoulder 1702 of the elongate shaft 1304.

When the retaining pins 1314 are clear of the shoulder 1702, the elongate shaft 1304 can be free to move axially relative to the housing 1302 (i.e., the release mechanism 1306 has been moved to the disengaged position). In addition, the biasing force provided by the elongate shaft biasing member 1318 can move the elongate shaft 1304 proximally as soon as the release mechanism moves to the disengaged position, thereby providing separation between the proximal flange 1710 of the elongate shaft 1304 and the base member 1312. This can provide a visual indication to a user that the desired depth of insertion has been reached, and can protect against further driving by retracting the elongate shaft 1304 away from the implant (e.g., pin 102) in the proximal direction. The elongate shaft biasing member 1318 can be selected to move the elongate shaft proximally by a desired distance. In some embodiments, the distance can be in a range of about 7 mm to about 10 mm.

The release mechanism 1306 can be reset to allow for multiple uses of the device. To move the release mechanism 1306 from the disengaged position to the engaged position, a user can remove any proximal force on the trigger element 1308 and apply a distal force to the proximal end of the elongate shaft 1304. If the user's supplied force overcomes the biasing force of the elongate shaft biasing member 1318, the elongate shaft will move distally relative to the housing 1302. When moving distally, the tapered face 1706 of the shoulder 1702 formed on the elongate shaft can contact the proximally sloped portion 1606 of the retaining pins 1314. As the shoulder slides by the pins 1314, the pins are forced away from the elongate shaft by the complementary slopes against the force of the biasing members 1514. After the shoulder 1702 of the elongate shaft 1304 clears the proximally sloped portion 1606, the pins can move toward the elongate shaft to seat the perpendicular face 1704 of the shoulder 1702 in the perpendicular cutouts 1602 of the pins 1314.

Figure 19:
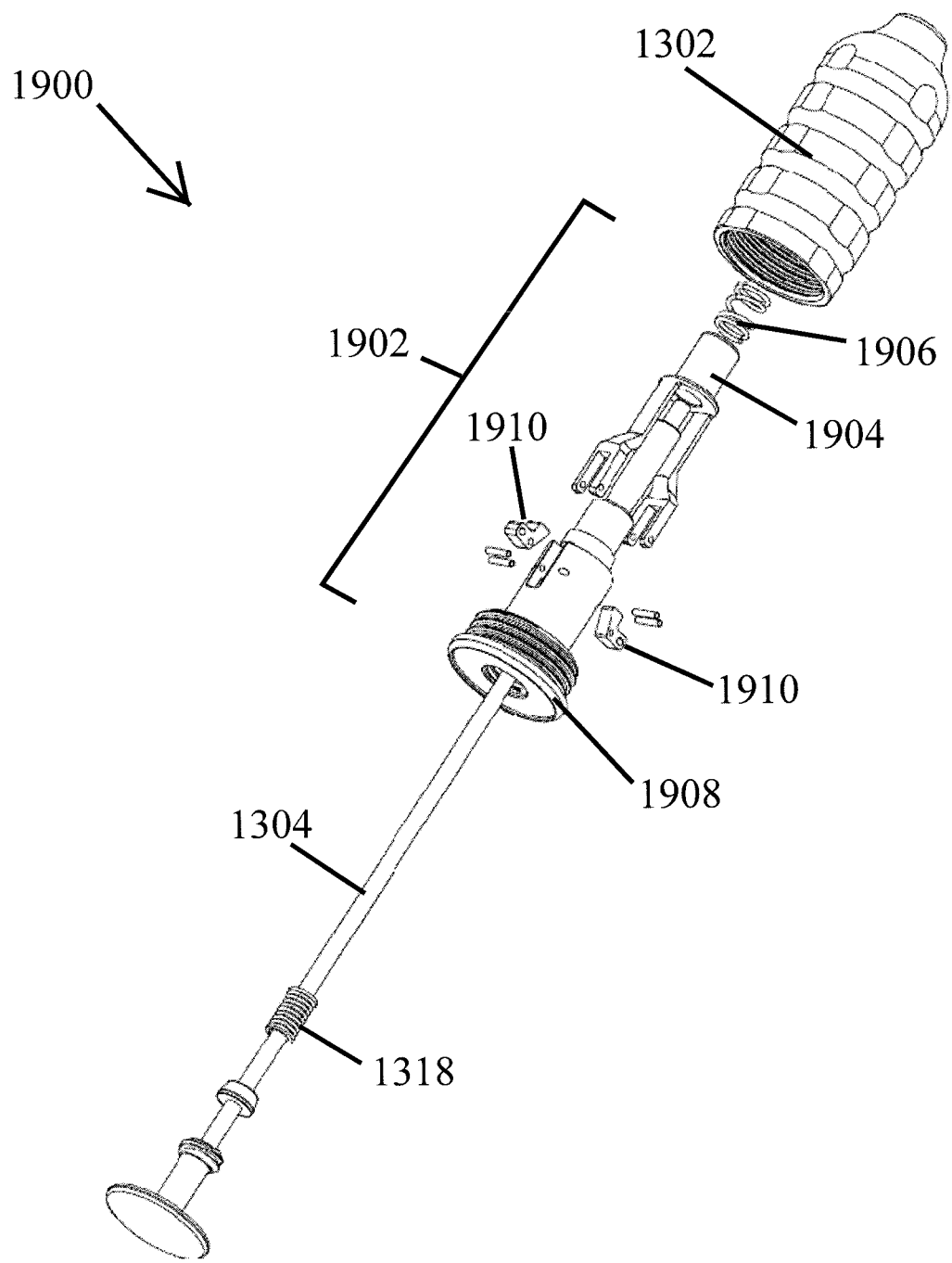
FIG. 19 is an exploded view of an alternative embodiment of a medical driver tool.

FIG. 19 illustrates an exploded view of another embodiment of a medical driver tool. The tool 1900 can include the housing 1302, elongate shaft 1304, and elongate shaft biasing member 1318 of the medical driver tool 1300. However, a release mechanism 1902 of the tool 1900 can utilize pivoting retaining pawls rather than retaining balls or biased retaining pins, as described above. In particular, the release mechanism 1902 can include a trigger element 1904, trigger element biasing member 1906, base member 1908, and a plurality of pivoting retaining pawls 1910.

Figure 20:
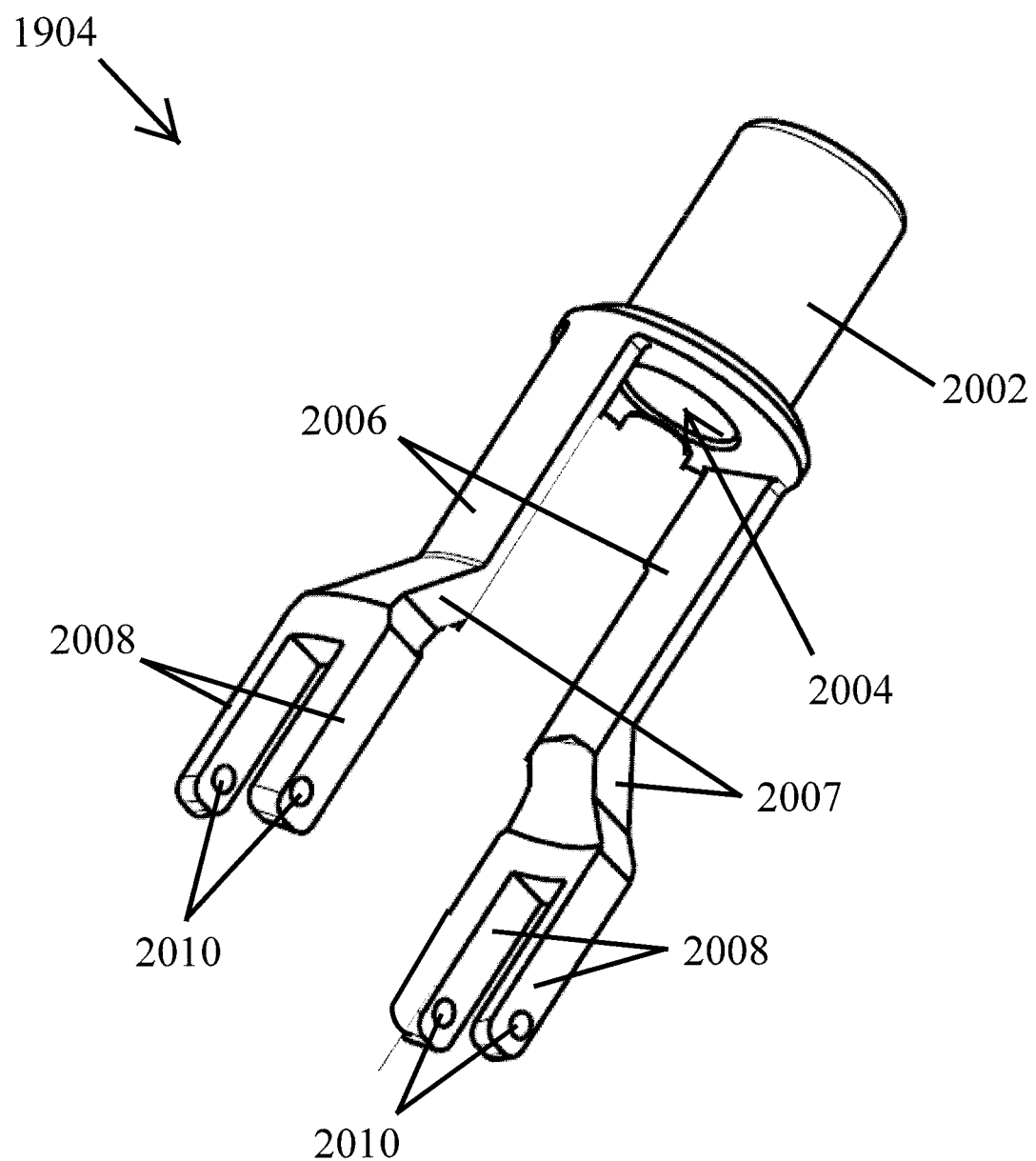
FIG. 20 is an illustration of a trigger element of the medical driver tool of FIG. 19.

With reference to FIG. 20, the trigger element 1904 can include a distal cylindrical portion 2002 having an inner lumen 2004 extending therethrough. This portion can be similar to the distal cylindrical portions 904 and 1402 of the trigger elements 608 and 1308. That is, the distal cylindrical portion 2002 can be sized to at least partially extend through the opening formed in the tapered end of the housing 1302. In addition, the distal cylindrical portion 2002 can have any of the alternative shapes discussed above, e.g., a flange formed on a distal end thereof configured to contact a patient's skin surface. In some embodiments, the distal cylindrical portion 2002 can have an outer diameter of about 8 mm and a length of about 12 mm. In addition, in certain embodiments, the inner lumen 2004 can have a diameter of about 5.6 mm. Further, a diameter of the trigger element 1904 can increase at a proximal end of the distal cylindrical portion 2002 in order to ensure that the trigger element 1904 cannot extend completely through the opening in the distal end of the housing 1302.

The trigger element 1904 can include a plurality of arms 2006 extending proximally from the distal cylindrical portion 2002. The number of arms 2006 can match the number of retaining pawls 1910 used in the tool 1900. The illustrated embodiment includes two arms 2006 that are positioned opposite one another along the circumference of the trigger element 1904. The arms 2006 can have a variety of shapes and sizes but, in some embodiments, the arms can have a rectangular cross section and can extend proximally such that the base member 1908 can be received therebetween without interference. In the illustrated embodiment, each arm 2006 includes an angled portion 2007 along its length that increases the space between the arms 2006 to accommodate the base member 1908. The length of the arms can vary according to the size of the tool 1900 and the particular geometry of the other components but, in some embodiments, the overall length of the trigger element (including the distal cylindrical portion) can be about 4.1 cm.

The distal end of each arm 2006 can include two opposed parallel fingers 2008 having a gap therebetween. The length and width of the gap can be sized to receive a retaining pawl 1910. In some embodiments, for example, the fingers 2008 can extend proximally for a length of about 8.4 mm, and the width of the gap between the fingers can be about 3.4 mm. At a proximal end of each of the fingers 2008, a borehole 2010 can extend therethrough such that a fixation pin 2120 (see FIG. 21) can be inserted through the borehole 2010 of both fingers. That is, the borehole 2010 can be formed along an axis extending through both fingers 2008 and, in some embodiments, the axis can be perpendicular to a longitudinal axis of the fingers (i.e., an axis extending in the proximal/distal direction) to ensure proper movement of a retaining pawl disposed within the gap between the fingers 2008. In some embodiments, the borehole 2010 can have a diameter of about 1.2 mm.

Figure 21:
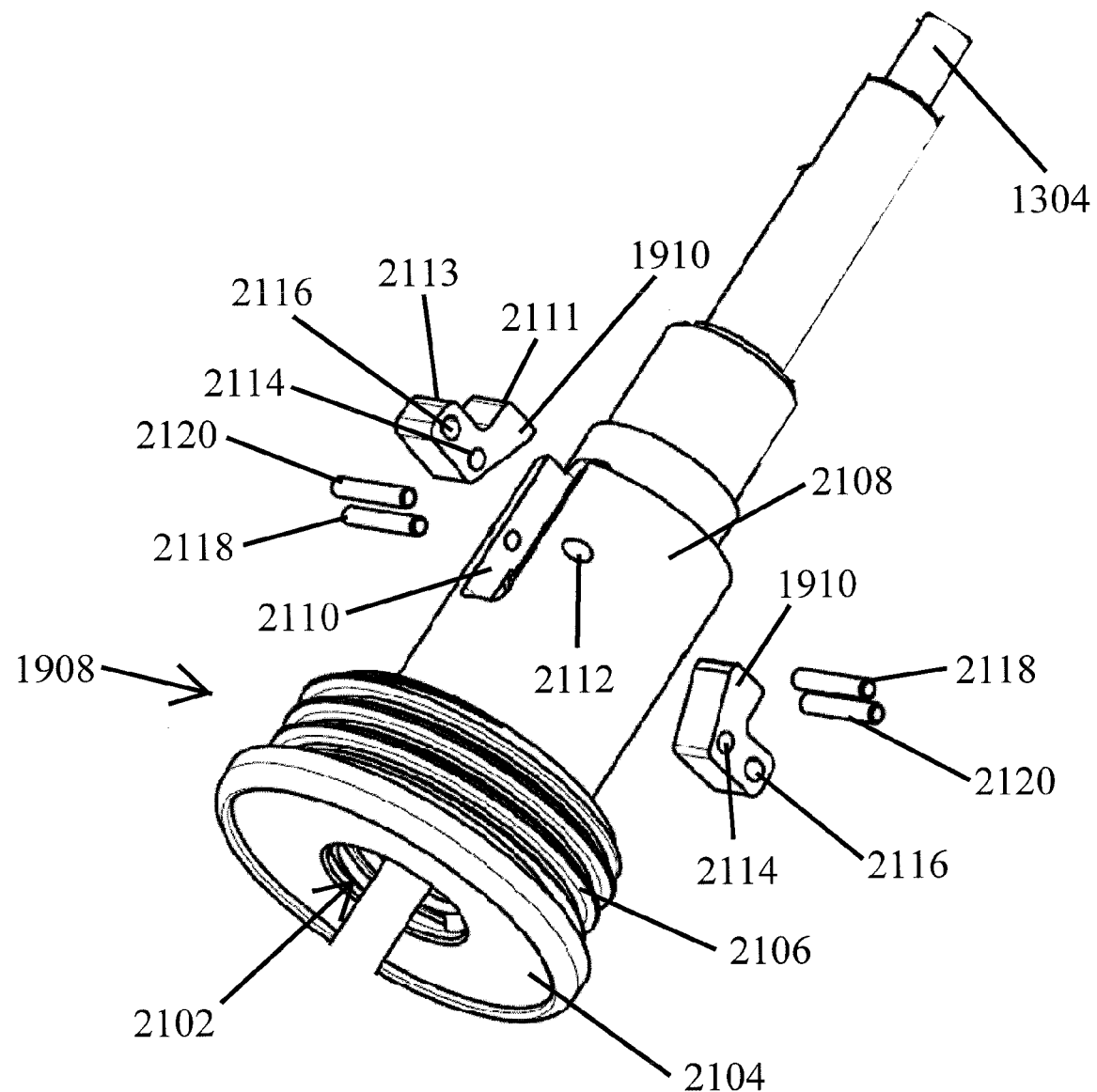
FIG. 21 is an illustration of a base member, retaining pawls, and fixation pins of the medical driver tool of FIG. 19.

The base member 1908 of the tool 1900 is shown in FIG. 21. The base member 1908 can have a similar profile to the base member 702 discussed above. In particular, the base member 1908 can include an inner lumen 2102 extending therethrough and can include several cylindrical portions having different diameters. At the proximal end of the base member 1908, a flange 2104 can be formed with a threaded coupling portion 2106 extending distally therefrom. A cylindrical portion 2108 extending proximally from the coupling portion 2106 can have an outer diameter less than diameters of both the coupling portion and the proximal flange 2104.

The cylindrical portion 2108 can include a plurality of channels 2110 (only one shown) formed therein and extending along a longitudinal axis of the base member 1908. The channels can extend through the sidewalls of the base member 1908 such that they are in communication with the inner lumen 2102. The number of channels 2110 can correspond to the number of retaining pawls 1910 in the tool 1900. Each channel 2110 can have a length and width sized to receive a retaining pawl 1910. In some embodiments, each channel 2110 can have a length of about 11.7 mm and a width of about 3.7 mm.

A plurality of boreholes 2112 (only one shown) can be formed in the cylindrical portion 2108 such that each borehole extends through the sidewalls of one of the channels 2110. The boreholes 2112 can be positioned such that a fixation pin 2118 can be placed through the borehole 2112 to provide a pivoting axis for a retaining pawl 1910. In some embodiments, the boreholes 2112 can have a diameter of about 1.2 mm.

Also shown in FIG. 21 are the retaining pawls 1910. Each retaining pawl 1910 can have an "L" shaped profile with that includes a shaft interfacing portion 2111 and a trigger coupling portion 2113 extending at an angle to one another and intersecting at a midpoint of the pawl. A borehole 2114 can be formed through retaining pawl 1910 near the midpoint thereof and can be configured to receive a fixation pin 2118 to pivotably couple the retaining pawl 1910 to the base member 1908. In some embodiments, the borehole 2114 can have a diameter of about 1.2 mm. When coupled to the base member 1908, the retaining pawl 1910 can be positioned at least partially within the channel 2110 such that the shaft interfacing portion 2111 can extend into the inner lumen 2102 of the base member 1908, and the trigger coupling portion 2113 can extend out of the channel 2110 away from the base member.

A second borehole 2116 can be formed in the trigger coupling portion 2113 of the retaining pawl 1910 and sized to receive a fixation pin 2120. The fixation pin 2120 can have a length and diameter sufficient to extend through the boreholes 2010 of each set of fingers 2008 on the trigger element 1904 to pivotably couple the retaining pawl 1910 to the trigger element 1904.

Figure 22:
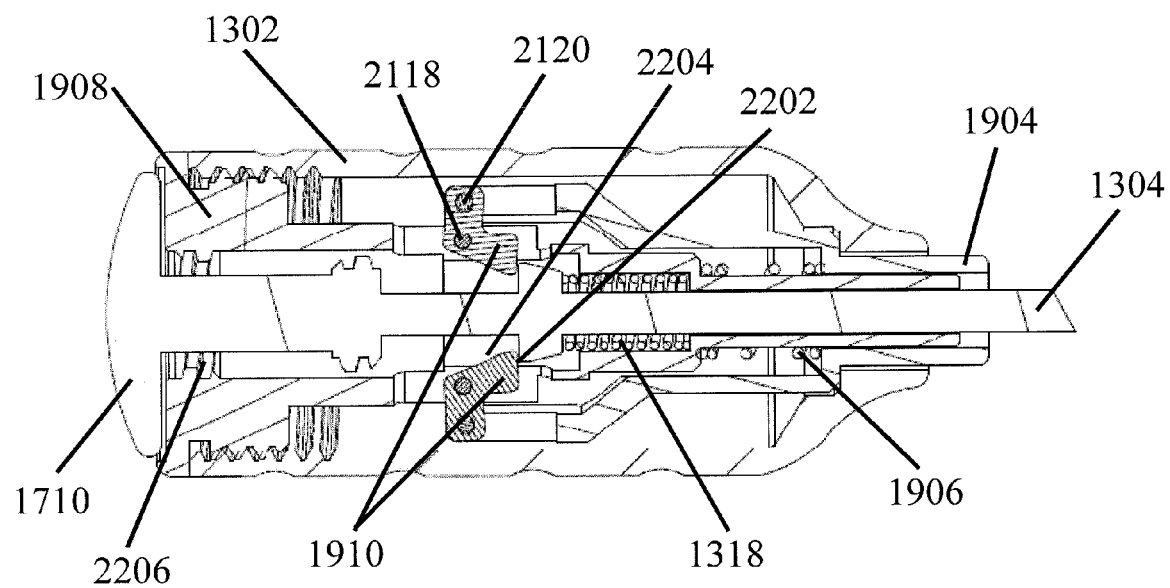
FIG. 22 is a cross-sectional view of the medical driver tool of FIG. 19.

FIG. 22 shows a portion of the assembled medical driver tool 1900 in cross-section. As shown in the figure, the trigger element 1904 is disposed within the housing 1302 and partially extends from the distal end of the housing through an opening formed therein. The base member 1908 is threadably coupled to the housing 1302 and extends through the inner lumen of the housing 1302 and the trigger element 1904. Further, the trigger element biasing member 1906 is positioned over a distal portion of the base member 1908 and biases the trigger element 1904 in a distal direction relative to the housing. The elongate shaft 1304 extends through the inner lumens of the housing 1302, the base member 1908, and the trigger element 1904 such that it extends distally from the housing. The elongate shaft biasing member 1318 is positioned over the elongate shaft 1304 and is compressed between the shoulder 1702 of the elongate shaft and a portion of the base member 1908 such that the elongate shaft is biased in a proximal direction relative to the housing 1302.

The trigger element 1904 is coupled to the base member 1908 by the plurality of retaining pawls 1910. In particular, each retaining pawl 1910 is positioned within a channel 2110 of the base member 1908 and pivotably coupled to the base member by a fixation pin 2118. Further, each retaining pawl 1910 is also positioned between a set of two fingers 2008 formed on the trigger element 1904 and pivotably coupled thereto by a fixation pin 2120. When the release mechanism 1902 is in the engaged position (as shown in FIG. 22), the shaft interfacing portion 2111 of each retaining pawl 1910 can extend into the inner lumen 2102 of the base member 1908 such that a distal face 2202 of the shaft interfacing portion 2111 can abut against the perpendicular face 1704 of the shoulder 1702 of the elongate shaft 1304. In addition, the proximal flange 1710 of the elongate shaft 1304 can abut against the proximal flange 2104 of the base member 1908. As a result, the elongate shaft 1304 can be restrained from moving axially (i.e., proximally or distally) relative to the housing 1302.

To actuate the release mechanism 1902 and move from an engaged position to a disengaged position in which the elongate shaft 1304 is free to move axially relative to the housing 1302, a proximal force can be applied to the trigger element 1904. If the proximal force is sufficiently strong to overcome the bias of the trigger element biasing member 1906, the trigger element can be moved in a proximal direction relative to the housing 1302. As the trigger element 1904 moves in a proximal direction relative to the housing, it will cause the retaining pawls 1910 to pivot around the fixation pin 2118 such that the trigger coupling portion 2113 moves proximally relative to the housing 1302 and the shaft interfacing portion 2111 moves away from the elongate shaft 1304. As this motion continues, the shaft interfacing portion 2111 will eventually clear the shoulder 1702 formed on the elongate shaft and the elongate shaft 1304 will be free to move axially relative to the housing 1302. Note that due to the pivoting motion of the retaining pawls 1910, the elongate shaft 1304 can be moved distally by a short distance during actuating of the release mechanism as the pawls pivot completely out of the inner lumen 2102 of the base member 1908. Accordingly, in some embodiments, the predetermined distance at which the release mechanism is actuated can be reduced by the potential amount of distal movement that the elongate shaft will experience during actuation. In some embodiments, this amount can be about 1 mm.

Furthermore, as soon as the shaft is free to move (i.e., the release mechanism is in the disengaged position), the biasing force from the elongate shaft biasing member 1318 can move the elongate shaft 1304 proximally relative to the housing 1302. This can cause the proximal flange 1710 of the elongate shaft 1304 to separate from the proximal flange 2104 of the base member 1908, thereby providing a visual indication to a user that a desired insertion depth has been reached. In addition, the proximal movement of the elongate shaft 1304 can bring a distal tip of the shaft out of contact with the implant being driven into bone. By creating space between the distal tip of the elongate shaft and the implant, additional impacting forces delivered to the elongate shaft can be prevented from driving the implant farther into bone. The amount of separation between the implant and the elongate shaft can be controlled by selecting the elongate shaft biasing member such that it can move the elongate shaft proximally by a desired distance. In some embodiments, this distance can be in a range of about 7 mm to about 10 mm.

To reset the release mechanism 1902 and move it back to an engaged position in which the elongate shaft 1304 is axially immovable relative to the housing 1302, a user can remove the proximal force on the trigger element 1904. This can allow the trigger element to move distally in response to a biasing force from the trigger element biasing member 1906. As the trigger element 1904 moves distally, the retaining pawls 1910 will pivot around the fixation pins 2118 such that the shaft interfacing portion 2111 of each retaining pawl 1910 is urged back into the inner lumen 2102 of the base member 1908 towards the elongate shaft 1304. A user can then apply a distal force to the proximal flange 1710 of the elongate shaft 1304 to move it distally relative to the housing 1302 against a biasing force from the elongate shaft biasing member 1318. As the elongate shaft 1304 moves distally, the distal-facing tapered face 1706 can contact and slide past a proximal-facing tapered face 2204 of the shaft interfacing portion 2111 of the retaining pawls 1910. Once the shoulder 1702 slides distally past the retaining pawls 1910, the distal face 2202 of the pawls can abut against the perpendicular face 1704 of the shoulder and restrain the elongate shaft from moving proximally relative to the housing 1302. A distance between the shoulder 1702 and the proximal flange 1710 of the elongate shaft can be selected such that the retaining pawls 1910 abut against the shoulder 1702 just as the proximal flange 1710 contacts the base member 1908 such that the shaft is restrained from moving axially (i.e., proximally or distally) relative to the housing 1302.

Also shown in FIG. 22 is a threaded portion 2206 of the inner lumen 2102 of the base member 1908. Threads formed along this portion can be configured to interface with the threaded portion 1708 of the elongate shaft 1304. The threaded portions 1708 and 2206 can serve the same purpose as the retaining ring 710 and flange 1106 described above. That is, once the elongate shaft 1304 is inserted into the inner lumen 2102 of the base member 1908, it cannot be removed by simply pulling the elongate shaft proximally. Rather, the elongate shaft 1304 will have to be rotated to back the threaded portion 1708 of the elongate shaft out through the threaded portion 2206 of the base member 1908. Accordingly, the threaded portions 1708 and 2206 can act as a stop to prevent the elongate shaft 1304 from moving too far in a proximal direction when the release mechanism is moved to a disengaged position and the elongate shaft biasing member 1318 moves the elongate shaft 1304. In addition, a user can remove the elongate shaft 1304 from the inner lumen of the base member 1908 for sterilization, repair, etc. by simply rotating the shaft through the threaded portion 2206. This can be easier than removing the retaining ring 710 to remove the elongate shaft 604.

Figure 1A:
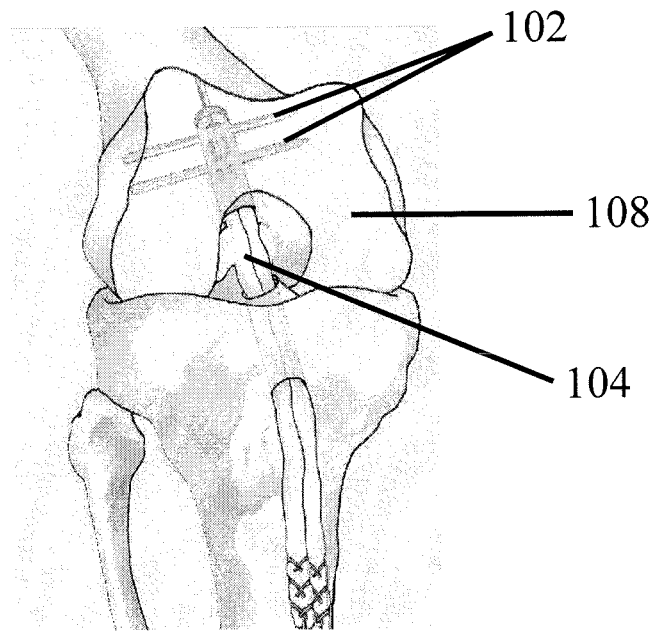
FIG. 1A is an illustration of a prior art soft tissue ligament graft in a knee.
Figure 1B:
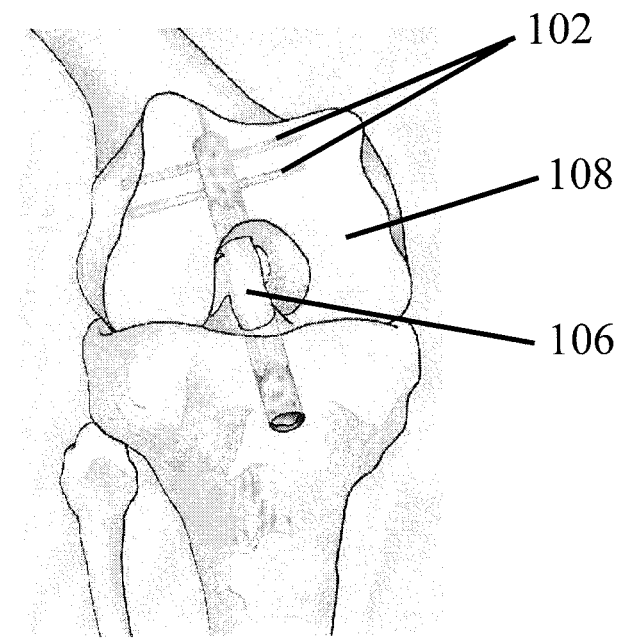
FIG. 1B is an illustration of a prior art bone-tendon-bone ligament graft in a knee.
Figure 2:
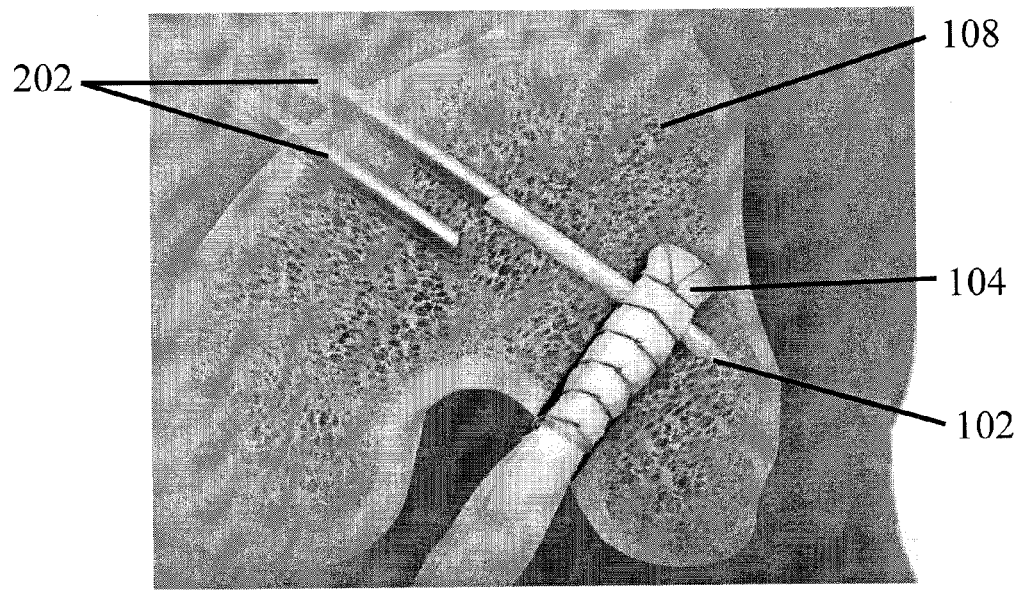
FIG. 2 is an illustration of a prior art pin securing a ligament graft in a bone tunnel.

With any embodiment of the medical driver tool described herein, a method for implanting an implant into bone can include applying a driving force to a proximal end of a housing, base member, elongate shaft, or other component of the driver tool to thereby drive an elongate shaft of the driver tool distally toward bone. For example, an implant can be driven into bone in the same manner discussed above and illustrated in FIGS. 2-4, but the medical driver tool described herein can be utilized in place of the driver shaft 302 shown in the figures. By way of further example, a user can grasp a driver tool, such as the driver tool 1900, around the housing 1302, insert its distal end into a delivery cannula 202, and strike the proximal end of the tool 1900 with a hammer or other impacting tool. Due to the release mechanism 1902 being in the engaged position wherein the elongate shaft 1304 cannot move axially (i.e., proximally or distally) relative to the housing 1302, the impacting force can be transferred to a distal end of the tool 1900 to drive an implant into bone.

When the implant is driven to a predetermined depth, a release mechanism of the driver tool can be automatically actuated to allow the elongate shaft to slide proximally relative to the housing. For example, as the implant is driven into bone, a proximal end of a delivery cannula 202 used to align the implant can approach the distal end of the housing of the driver tool 1900. As the implant reaches the predetermined depth, the proximal end of the delivery cannula 202 can come into contact with the distal end of the trigger element 1904 and apply a proximal force thereto. The proximal force can overcome a biasing force of the trigger element biasing member 1906 and move the trigger element proximally relative to the housing 1302 by a distance, e.g., about 1 mm. This movement can rotate the retaining pawls 1910 out of the inner lumen 2102 of the base member 1908 such that the elongate shaft 1304 can freely move relative to the housing 1302.

In some embodiments, actuating the release mechanism can also include moving the elongate shaft proximally relative to the housing. This can be accomplished, for example, by the biasing force from the elongate shaft biasing member 1318. In some embodiments, the proximal movement of the elongate shaft 1304 can provide a visual indication to a user that the predetermined depth has been reached. In addition, proximal movement of the elongate shaft 1304 can create separation between a distal end of the elongate shaft and a proximal end of the implant being driven into bone. As a result, even if a user ignores the visual indication and delivers a subsequent impacting force to the tool 1900, the implant will not be driven further into bone. Rather, the subsequent force can drive the elongate shaft 1304 distally relative to the housing 1302 to close the gap between the distal end of the elongate shaft and the implant, but the implant will not be driven farther into bone.

The devices described herein can be formed from any of a variety of biocompatible materials. Suitable biocompatible materials can include, for example, metals such as stainless steel and titanium. Other materials, such as polymers, may also be used, provided the material can withstand the impacting forces delivered to drive an implant into bone. In addition, in certain embodiments particular components of a medical driver tool can be made from one material while other components can be made from a different material.

The devices disclosed herein can be designed for multiple uses and can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, in an exemplary embodiment a medical driver tool, such as the tool 1900, can be disassembled after use for cleaning and selective replacement of parts. For example, the release mechanism 1902 can be actuated to move from the engaged position to the disengaged position, and the elongate shaft 1304 can be pulled proximally (and rotated through the threaded portion 2206 of the base member 1908) to remove the elongate shaft and the elongate shaft biasing member 1318 from the inner lumen of the base member. The base member 1908 can be decoupled from the housing 1302 by rotating the two components relative to one another. This can allow the base member 1908 and trigger element 1904 to be removed from the housing 1302. If further disassembly is required, the fixation pins 2118 and 2120 can be removed to separate the base member 1908 from the retaining pawls 1910 and trigger element 1904.

Preferably, the devices described herein will be processed before surgery. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. In other embodiments, sterilization can be performed using any number of ways known to those skilled in the art including beta or gamma radiation, ethylene oxide, steam, or a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A medical driver tool, comprising:
   a housing having proximal and distal ends, the proximal end being configured to receive an impacting force;
   an elongate shaft extending at least partially through the housing and extending distally from the housing, the elongate shaft having a distal tip configured to drive an implant into bone; and
   a release mechanism coupled between the housing and the elongate shaft, the release mechanism having an engaged position in which the elongate shaft is axially immovable relative to the housing, and a disengaged position in which the elongate shaft is axially movable relative to the housing, the release mechanism being configured to move from the engaged position to the disengaged position in response to a force applied to move at least a portion of the release mechanism proximally relative to the housing.

2. The tool of claim 1, wherein the release mechanism includes a plurality of retaining balls spaced radially around the elongate shaft and seated within a detent formed in an outer surface of the elongate shaft.

3. The tool of claim 1, wherein the release mechanism includes a plurality of biased retaining pins that engage a shoulder formed on the elongate shaft.

4. The tool of claim 1, wherein the release mechanism includes a plurality of pivoting retaining pawls that engage a shoulder formed on the elongate shaft.

5. The tool of claim 1, wherein the release mechanism is configured to move the elongate shaft proximally relative to the housing when moving from the engaged position to the disengaged position.

6. The tool of claim 5, wherein the elongate shaft is moved proximally by about 10 mm.

7. The tool of claim 1, wherein the release mechanism includes a trigger element extending distally from the housing, the trigger element being movable relative to the housing.

8. A medical implant and delivery system, comprising:
   a biocompatible implant configured to be implanted in bone; and
   a driver tool having
      a housing with proximal and distal ends, the proximal end being configured to receive an impacting force;
      an elongate shaft extending at least partially through the housing and extending distally from the housing, the elongate shaft having a distal tip configured to drive the biocompatible implant into bone;
      a release mechanism coupled between the housing and the elongate shaft, the release mechanism being configured to move from an engaged position in which the elongate shaft is axially immovable relative to the housing to a disengaged position in which the elongate shaft is axially movable relative to the housing in response to a force applied to move at least a portion of the release mechanism proximally relative to the housing.

9. The system of claim 8, further comprising a delivery cannula configured to receive the biocompatible implant and a distal portion of the elongate shaft of the driver tool.

10. The system of claim 9, wherein the release mechanism of the driver tool includes a trigger element configured to contact a proximal end of the delivery cannula.

11. The system of claim 8, further comprising an impactor configured to impart a force to the proximal end of the driver tool housing.

12. The system of claim 8, wherein the release mechanism includes a plurality of retaining balls spaced radially around the elongate shaft and seated within a detent formed in an outer surface of the elongate shaft.

13. The system of claim 8, wherein the release mechanism includes a plurality of biased retaining pins that engage a shoulder formed on the elongate shaft.

14. The system of claim 8, wherein the release mechanism includes a plurality of pivoting retaining pawls that engage a shoulder formed on the elongate shaft.

15. A method for implanting an implant in bone, comprising:
   applying a driving force to a proximal end of a housing on a driver tool to thereby drive an elongate shaft of the driver tool distally toward bone;
   wherein a release mechanism of the driver tool is actuated in response to the implant reaching a predetermined depth to allow the elongate shaft to slide proximally relative to the housing.

16. The method of claim 15, wherein actuation of the release mechanism occurs in response to application of a force to a trigger element of the release mechanism to move the trigger element proximally relative to the housing.

17. The method of claim 16, wherein the release mechanism is actuated by the trigger element contacting a proximal end of a delivery cannula.

18. The method of claim 15, wherein actuating the release mechanism includes moving the elongate shaft proximally relative to the housing.

19. The method of claim 15, wherein applying a driving force includes impacting a proximal end of the housing with a hammer.

* * * * *